United States Patent
Zhang et al.

(10) Patent No.: US 12,319,644 B2
(45) Date of Patent: Jun. 3, 2025

(54) LIPID COMPOUND CONTAINING CARBAMATE BOND AND APPLICATIONS THEREOF

(71) Applicant: RONGCAN (SHANGHAI) BIOTECH CO., LTD., Shanghai (CN)

(72) Inventors: Xueqing Zhang, Shanghai (CN); Yilong Teng, Shanghai (CN); Bin Zhang, Shanghai (CN); Xing Zheng, Shanghai (CN)

(73) Assignee: Rongcan (Shanghai) Biotech Co., Ltd., Shanghai (CN)

( * ) Notice: Subject to any disclaimer, the term of this patent is extended or adjusted under 35 U.S.C. 154(b) by 0 days.

(21) Appl. No.: 18/714,848

(22) PCT Filed: Nov. 17, 2023

(86) PCT No.: PCT/CN2023/132430
§ 371 (c)(1),
(2) Date: May 30, 2024

(87) PCT Pub. No.: WO2024/109665
PCT Pub. Date: May 30, 2024

(65) Prior Publication Data
US 2025/0002451 A1    Jan. 2, 2025

(30) Foreign Application Priority Data
Nov. 21, 2022 (CN) .......................... 202211461172.X

(51) Int. Cl.
| | |
|---|---|
| *C07C 271/20* | (2006.01) |
| *A61K 9/51* | (2006.01) |
| *A61K 45/06* | (2006.01) |
| *A61K 47/18* | (2017.01) |

(52) U.S. Cl.
CPC .............. *C07C 271/20* (2013.01); *A61K 9/51* (2013.01); *A61K 45/06* (2013.01); *A61K 47/18* (2013.01)

(58) Field of Classification Search
CPC ........ C07C 271/20; A61K 9/51; A61K 45/06; A61K 47/18
See application file for complete search history.

(56) References Cited

U.S. PATENT DOCUMENTS

| | | | |
|---|---|---|---|
| 11,130,741 B2 | 9/2021 | Kirsebom et al. | |
| 11,472,766 B2 | 10/2022 | Ying | |
| 2016/0159940 A1 | 6/2016 | Rannard et al. | |
| 2024/0342088 A1* | 10/2024 | Weng | C08G 65/332 |

FOREIGN PATENT DOCUMENTS

| | | | |
|---|---|---|---|
| CN | 88100804 A | | 8/1988 |
| CN | 105451772 A | | 3/2016 |
| CN | 109641889 A | | 4/2019 |
| CN | 113402405 | * | 9/2021 |
| CN | 113402405 A | | 9/2021 |
| CN | 114206827 A | | 3/2022 |
| CN | 115947671 A | | 4/2023 |
| WO | 201718842 A1 | | 7/2017 |
| WO | WO2019/016819 | * | 1/2019 |

OTHER PUBLICATIONS

CN113402405 translation (Year: 2021).*
International Search Report & Written Opinion issued in PCT/CN2023/132430, mailed Jan. 16, 2024 [8 pages].
First Office Action (w/translation) issued in CN Application No. 202211461172, dated May 23, 2023 [13 pages].
Mathias B. Danielsen, et al., "Polyamine-Functionalized 2'-Amino-LNA in Oligonucleotides: Facile Synthesis of New Monomers and High-Affinity Binding towards ssDNA and dsDNA," Chemistry—A European Journal, 2021, vol. 27 [7 pages].

* cited by examiner

*Primary Examiner* — Yevgeny Valenrod
*Assistant Examiner* — Blaine G Doletski
(74) *Attorney, Agent, or Firm* — IceMiller LLP

(57) ABSTRACT

The present invention belongs to the field of biomedicine, which discloses a class of lipid compounds containing carbamate bond and applications thereof. The lipid compounds have the following structures:

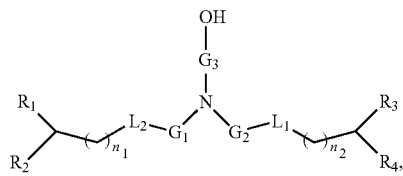

wherein the definitions of the various groups are described in the specification. The lipid nanoparticulate carriers prepared from the compounds described in the present invention exhibit excellent biocompatibility and safety as well as unexpected improvements in transfection efficiency, making them suitable for biomedical industrialization.

14 Claims, 4 Drawing Sheets

LIPID COMPOUND CONTAINING CARBAMATE BOND AND APPLICATIONS THEREOF

CROSS-REFERENCE TO RELATED APPLICATIONS

This application is a National Stage of International Patent Application No. PCT/CN2023/132430, filed on Nov. 17, 2023, which claims priority to Chinese Patent Application No. CN 202211461172.X, filed on Nov. 21, 2022, the disclosures of which are incorporated by reference in their entireties.

TECHNICAL FIELD

The present invention relates to the field of biomedicine, particularly a class of lipid compounds containing carbamate bond (—NH(C=O)O— or —O(C=O)NH—) and applications thereof.

BACKGROUND

Gene therapy is a treatment method that aims to correct or compensate for diseases caused by defective or abnormal genes by introducing exogenous genes into target cells. Nucleic acid vaccines, also known as genetic vaccines, refers to the encoding immunogenic protein or peptide nucleic acid sequence (such as DNA, mRNA, etc.) into the host. These sequences are then expressed by the host cells, resulting in the production of immunogenic proteins or polypeptides, inducing host cells to produce immune response to the immunogen, in order to achieve the purpose of prevention and treatment of disease. The success of both gene therapy and genetic vaccines heavily relies on the effective delivery of exogenous genes. Among various methods for gene delivery, the development of suitable lipid nanoparticles (LNPs) for encapsulating nucleic acids, targeting them to the desired cells, and delivering specific genes into the cells has gradually been adopted by scientists.

An obvious difference between nucleic acid drugs and traditional chemical drugs is that the nucleic acid drugs have a large number of phosphate groups, resulting in a negative charge and a high molecular weight. In order to enable their better encapsulation by LNPs, various lipid compounds such as ionizable lipids have been developed.

The lipid compounds containing carbamate bond (—NH(C=O)O— or —O(C=O)NH—) described in this invention may exhibit charge-altering properties with variations in environmental pH. It carries a positive charge at acidic pH and remains neutral at physiological pH. The physicochemical properties and concentration of this compound alter the surface charge of LNPs under different pH conditions. This charge state significantly influences immune recognition, blood clearance, distribution in the blood and tissue, and the ability to escape from endosomes within cells. These factors are crucial for intracellular delivery of nucleic acids.

"Lipid nanoparticle (LNP)" refers to a nanostructure formed by encapsulating or associating therapeutic agents like nucleic acids with lipid compounds, including ionizable lipid compounds. This nanostructure exhibits a bilayer or multilayer membrane structure. Ionizable lipid compounds, other lipid excipients, and the nucleic acids encapsulated in nanoparticles are distributed within the nanoparticles. LNP and its compositions can be used for a diverse range of applications, including the in vitro and in vivo delivery of encapsulated or integrated (e.g., complexed) therapeutic agents, such as nucleic acids, into cells to induce the expression of target proteins or peptides or to inhibit the expression of target genes.

The development of LNP has overcome several challenges that hinder the clinical application of nucleic acid drugs. These challenges include: firstly, nucleic acid molecules are easily degraded by nucleases existing in the body or in nature; secondly, the ability of nucleic acid molecules to enter cells, interact with target organelles, and regulate the expression of target genes or proteins is limited; and thirdly, the efficiency of intracellular delivery is low, such as the inability to escape from endosomes.

The core of nucleic acid delivery primarily comprises a carrier and mRNA, and the carrier's key component is ionizable lipids. An ionizable lipid molecule capable of overcoming the aforementioned challenges is essential for the delivery of nucleic acids. Although commercially available ionizable lipid compounds have achieved significant success, there are still various issues, such as the side effects of increased dosage of lipid compounds due to the low delivery efficiency. To enhance the delivery efficiency of nucleic acids and increase the safety of LNP, this invention provides a new class of ionizable lipid compounds containing carbamate bond (—NH(C=O)O— or —O(C=O)NH—) to solve these challenges.

SUMMARY OF THE INVENTION

To solve the limitations of the prior art, the objective described in this invention is to provide a new class of ionizable lipid compounds containing carbamate bond (—NH(C=O)O— or —O(C=O)NH—) and applications thereof. The mRNA-LNPs prepared using these novel ionizable lipid compounds exhibit high nucleic acid transfection efficiency, excellent biocompatibility and high stability.

In order to achieve the aforementioned object, the technical solution described in the present invention is as follows:

A lipid compound, wherein the compound is of the following structure:

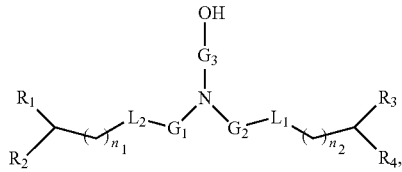

$n_1$ and $n_2$ are each independently 0, 1, 2, 3, 4, 5, 6, 7, 8, 9, or 10;

$G_1$ and $G_2$ are each independently C1-C10 alkylene;

$R_1$, $R_2$, $R_3$ and $R_4$ are each independently H, C1-C20 linear or branched alkyl, or C2-C20 linear or branched alkenyl;

$G_3$ is C1-C10 alkylene; or $G_3$ is $(CH2)_a$—O—$(CH2)_b$, wherein a and b are each independently 1, 2, 3, 4, 5, 6, 7, 8, or 9, and a+b is an integer from 2 to 10;

$L_1$ is —(C=O)O—, —O(C=O)—, —NH(C=O)O—, —O(C=O)NH—, or —O(C=O)O—;

$L_2$ is —NH(C=O)O— or —O(C=O)NH—.

The lipid compounds described in this invention feature a tertiary amine-containing group in the head structure and two hydrophobic groups in the tail structure. One hydrophobic group contains —(C=O)O—, —O(C=O)—, —NH(C=O)O—, —O(C=O)NH— or —O(C=O)O—, while the other one contains carbamate bond (—NH(C=O)O— or —O(C=O)NH—) as a degradable moiety. This molecular structure allows the formation of hydrogen bonds between the two tails in a buffered solution, further forming a three-dimensional cone-shaped structure. The aforementioned structure confers capacities of fusing membrane, escaping endosome and mediating transfection to the corresponding LNPs. Any improvements of the lipid molecules based on the aforementioned structure fall within the scope of protection of the invention and are inspired by the invention.

The aforementioned lipid compound, as an embodiment, —CH(R$_1$)R$_2$ and —CH(R$_3$)R$_4$ are each independently selected from an one of the group consisting of

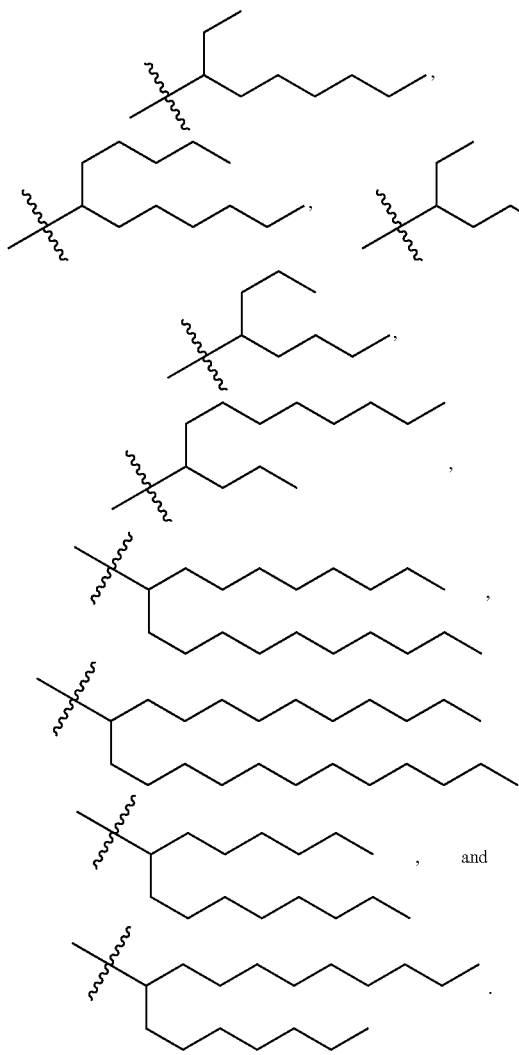

It should be noted that the structure of the hydrophobic groups is not limited. Compounds with a tertiary amine-containing group in the head structure and two hydrophobic groups in the tail structure. One hydrophobic group is modified with —(C=O)O—, —O(C=O)—, —NH(C=O)O—, —O(C=O)NH— or —O(C=O)O—, while the other one is incorporated with carbamate bond (—NH(C=O)O— or —O(C=O)NH—) as a degradable moiety fall all within the scope of this invention.

The aforementioned lipid compound, as an embodiment, —CH(R$_1$)R$_2$ and —CH(R$_3$)R$_4$ are each independently selected from any one of the group consisting of

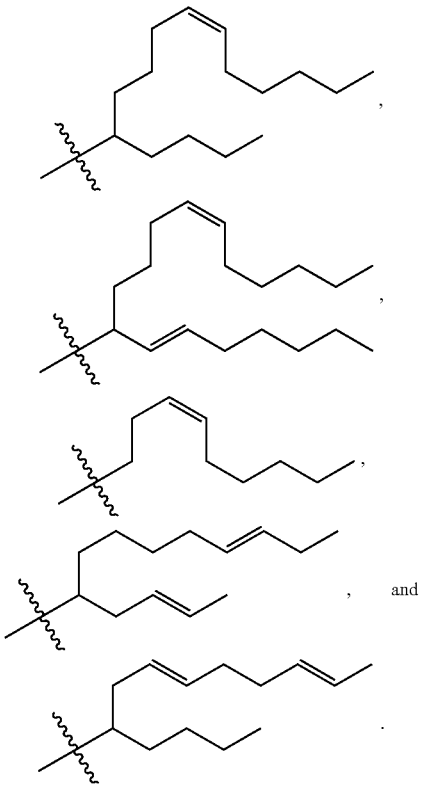

, and

It should be noted that the structure of the hydrophobic groups is not limited. Compounds with a tertiary amine-containing group in the head structure and two hydrophobic groups in the tail structure. One hydrophobic group is modified with —(C=O)O—, —O(C=O)—, —NH(C=O)O—, —O(C=O)NH— or —O(C=O)O—, while the other one is incorporated with carbamate bond (—NH(C=O)O— or —O(C=O)NH—) as a degradable moiety fall all within the scope of this invention.

The aforementioned lipid compound, as an embodiment, —CH(R$_1$)R$_2$ and —CH(R$_3$)R$_4$ are each independently selected from any one of the group consisting of

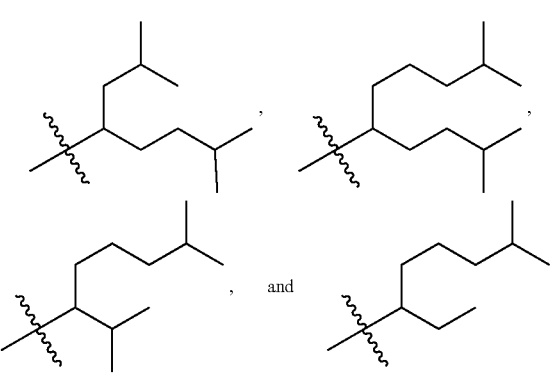

, and

It should be noted that the structure of the hydrophobic groups is not limited. Compounds with a tertiary amine-containing group in the head structure and two hydrophobic groups in the tail structure. One hydrophobic group is modified with —(C=O)O—, —O(C=O)—, —NH(C=O)O—, —O(C=O)NH— or —O(C=O)O—, while the other one is incorporated with carbamate bond (—NH(C=O)O— or —O(C=O)NH—) as a degradable moiety fall all within the scope of this invention.

In the most preferable embodiment, the aforementioned lipid compound is selected from the group consisting of:

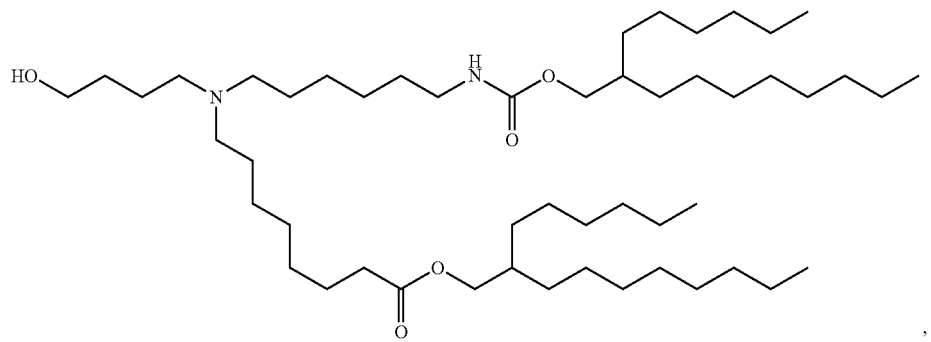

,

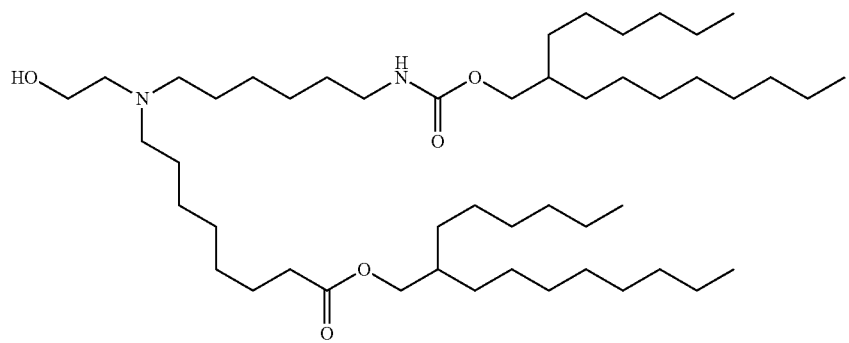

,

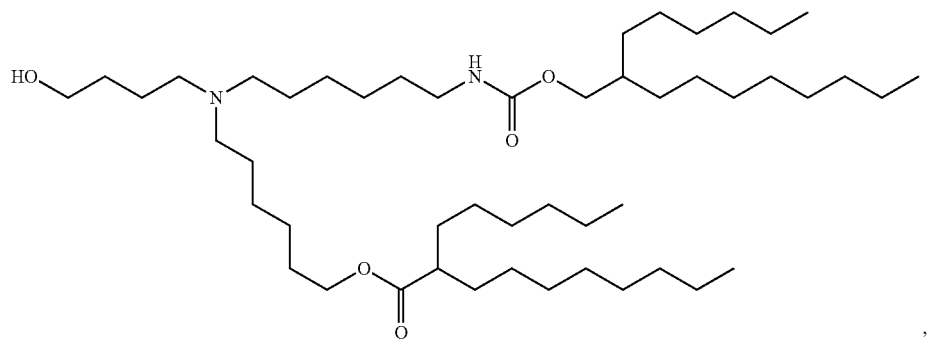

,

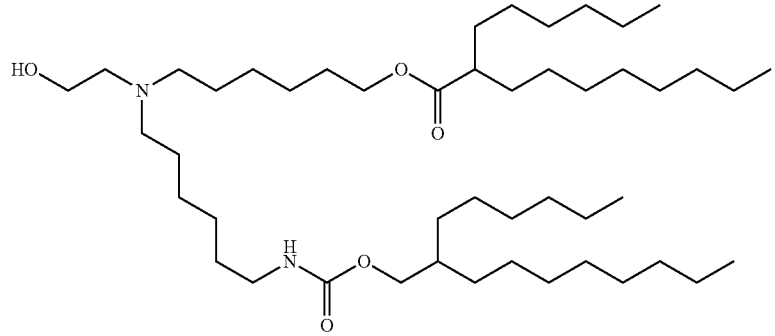

,

-continued
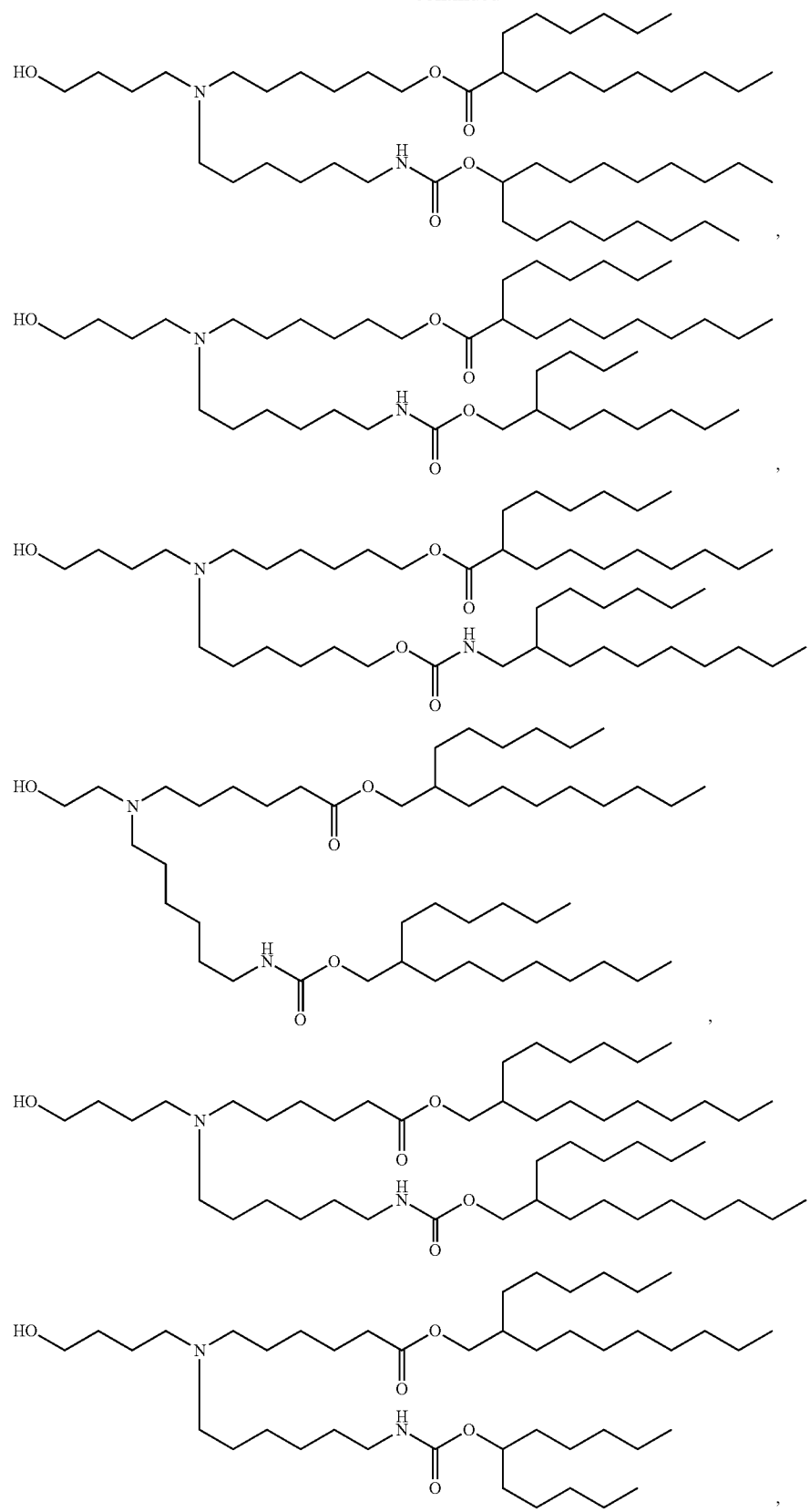

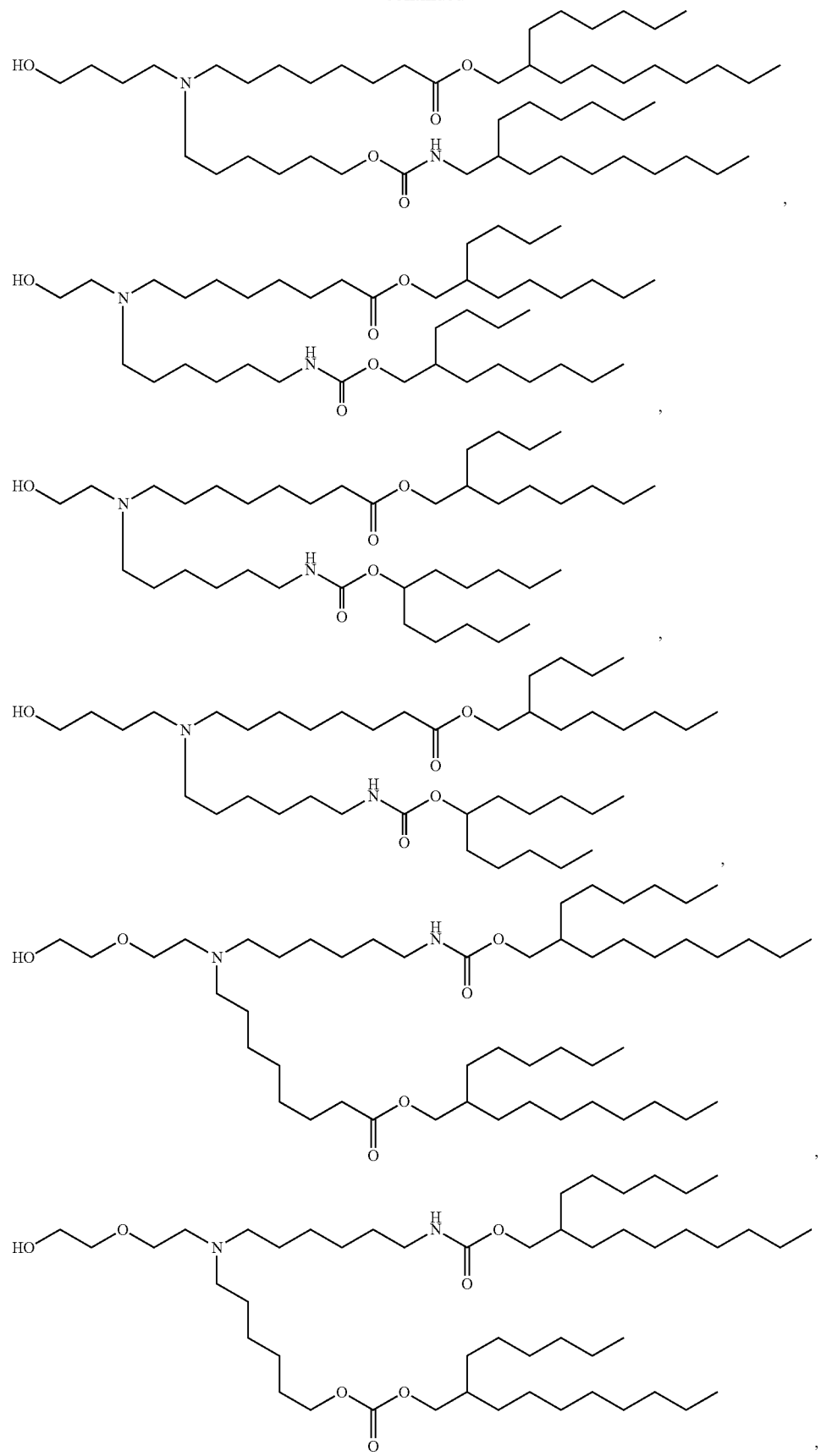

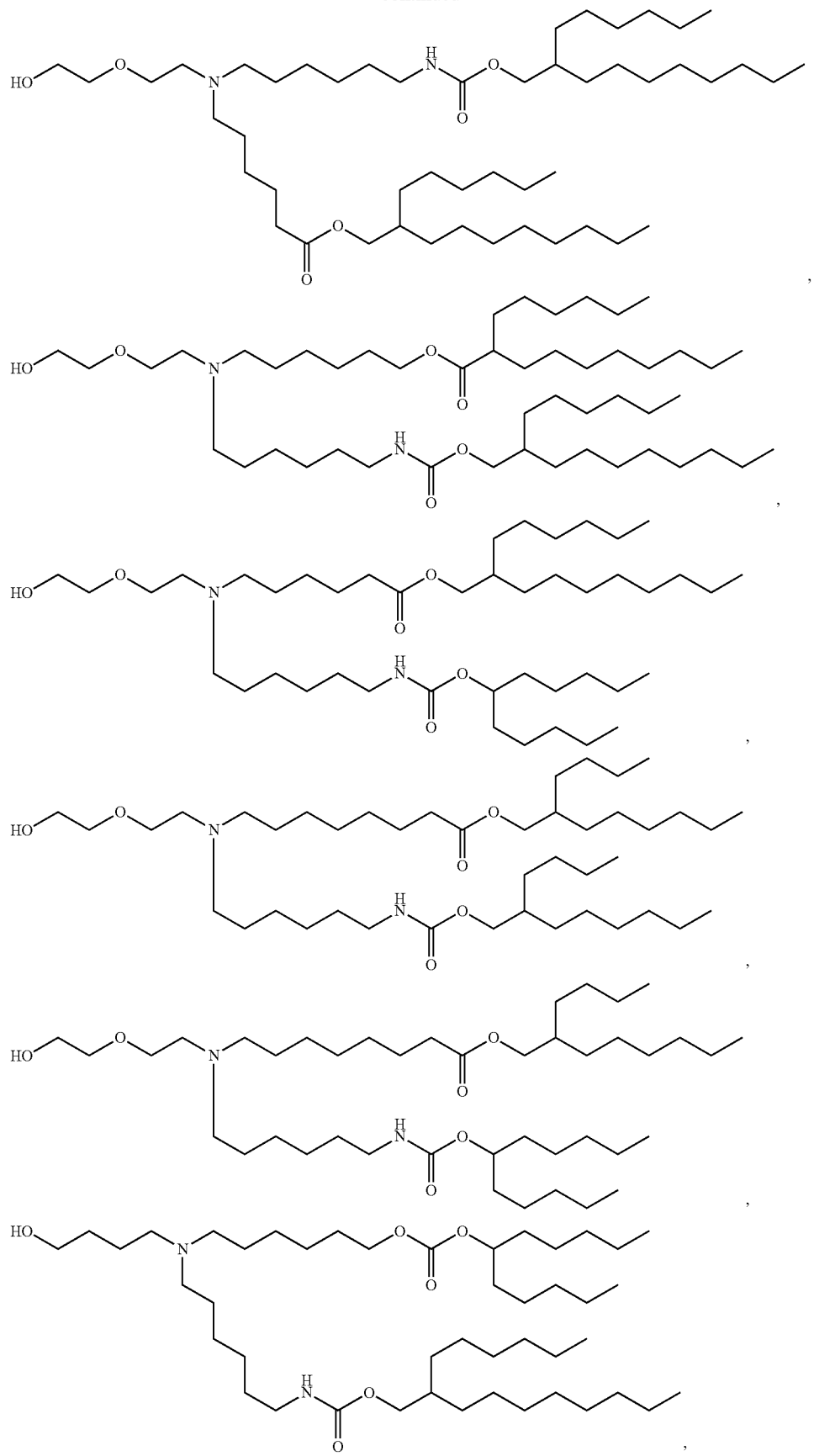

-continued

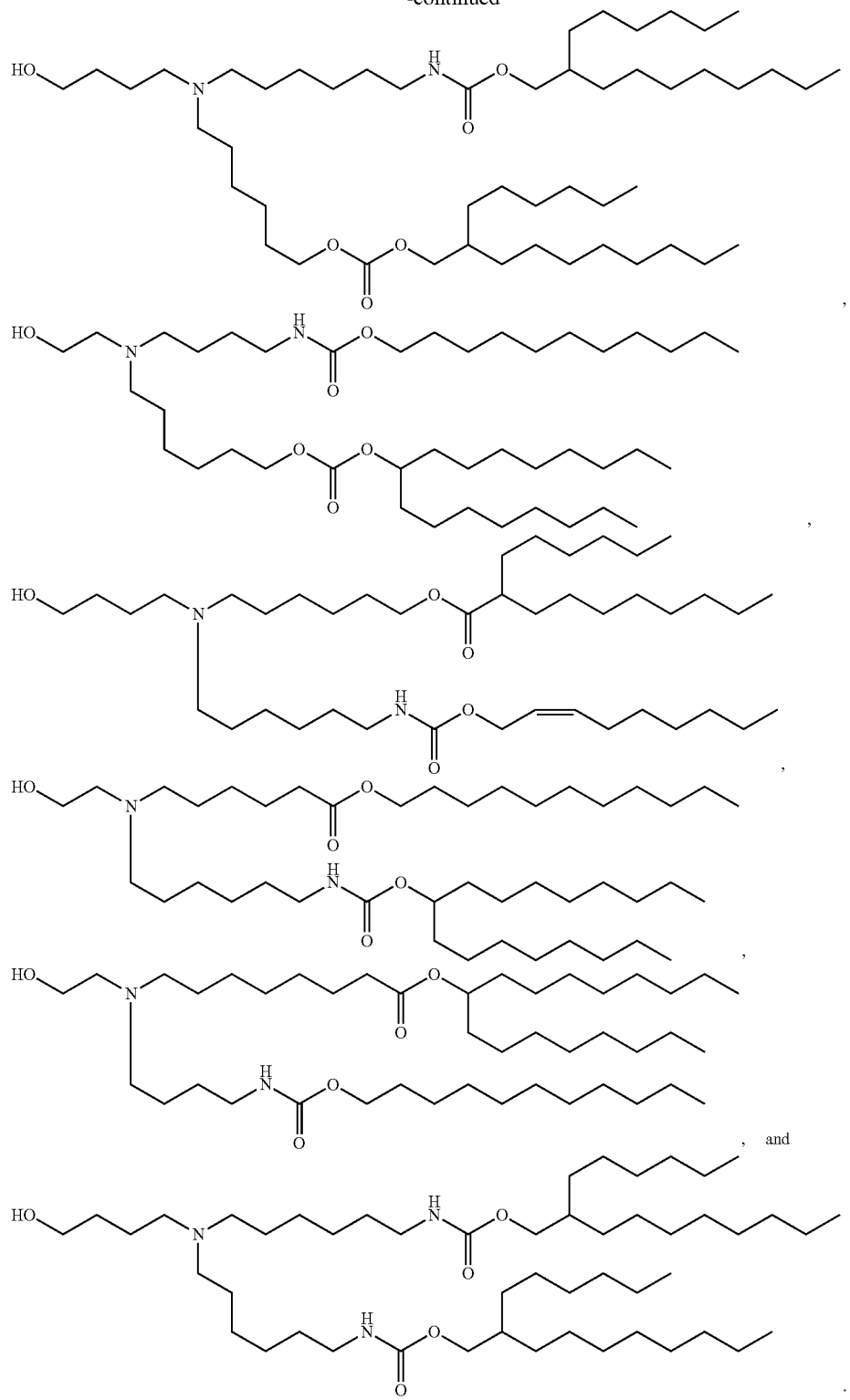

, and

A composition, wherein comprises the composition of the aforementioned lipid compound, or a stereoisomer, tautomer, or pharmaceutically acceptable salt thereof.

The aforementioned composition, wherein the composition comprises any ingredients selected from the group consisting of carriers, loaded drugs, pharmaceutical adjuvants, or the combinations thereof.

The aforementioned composition, wherein the carrier comprises one or more ingredients selected from the group consisting of lipid compounds, helper lipids, structural lipids, polymer-conjugated lipids or amphiphilic block copolymers, or combinations thereof. It should be noted that the carrier composition is not limited, and can be a combination of existing known substances or unknown substances, as long as the lipid compounds having the structures described in the present invention fall within the protection scope of the present invention, and they can all be inspired by the present invention.

The aforementioned composition, wherein as an embodiment, the molar ratio of the aforementioned lipid compound to helper lipid ranges from 0.5:1 to 15:1.

The aforementioned composition, wherein as an embodiment, the molar ratio of the aforementioned lipid compound to structural lipid ranges from 0.5:1 to 5:1.

The aforementioned composition, wherein as an embodiment, the molar ratio of the aforementioned lipid compound to the polymer-conjugated lipid ranges from 5:1 to 250:1.

The aforementioned composition, wherein as an embodiment, the molar ratio of the aforementioned lipid compound to the amphiphilic block copolymer ranges from 1:1 to 200:1.

The aforementioned composition, wherein the carrier is lipid nanoparticles, and the average size of the lipid nanoparticles ranges from 30 to 200 nm, and the polydispersity index of the lipid nanoparticle is ≤0.3.

The aforementioned compositions, wherein the loaded drugs comprise one or more nucleic acid molecules, small molecule compounds, peptides, or proteins. The examples are not exhaustive, as long as lipid compounds with the structure described in the present invention are used, regardless of the drug applied, they fall within the protective scope of the present invention and are inspired by this invention.

The aforementioned composition, wherein the pharmaceutical adjuvants comprise one or more diluents, stabilizers, preservatives, or lyoprotectants. The examples are not exhaustive, as long as lipid compounds with the structure described in the present invention are used, regardless of the pharmaceutical adjuvant compound applied, they fall within the protective scope of the present invention and are inspired by this invention.

The advantages of the present invention are as follows:

The lipid compounds described in this invention feature a tertiary amine-containing group in the head structure and two hydrophobic groups in the tail structure. One hydrophobic group is modified with —(C=O)O—, —O(C=O)—, —NH(C=O)O—, —O(C=O)NH— or —O(C=O)O—, while the other one is incorporated with carbamate bond (—NH(C=O)O— or —O(C=O)NH—) as a degradable moiety. This molecular structure allows the formation of hydrogen bonds between the two tails in a buffered solution, further forming a three-dimensional cone-shaped structure. The aforementioned structure confers capacities of fusing membrane, escaping endosome and mediating transfection to the corresponding LNPs, thereby leading to superior protein expression capability.

The carbamate bond (—NH(C=O)O— or —O(C=O)NH—) is incorporated as a degradable moiety in the lipid compounds described in this invention, which confer good biocompatibility to the corresponding LNPs.

The lipid compounds containing the molecular structures as described in this invention possess high transfection efficiency, good safety profile and biocompatibility. Additionally, these lipid compounds are easy-to-synthesize, making them suitable for biomedical applications.

TERMS AND ABBREVIATIONS

Figure 1:
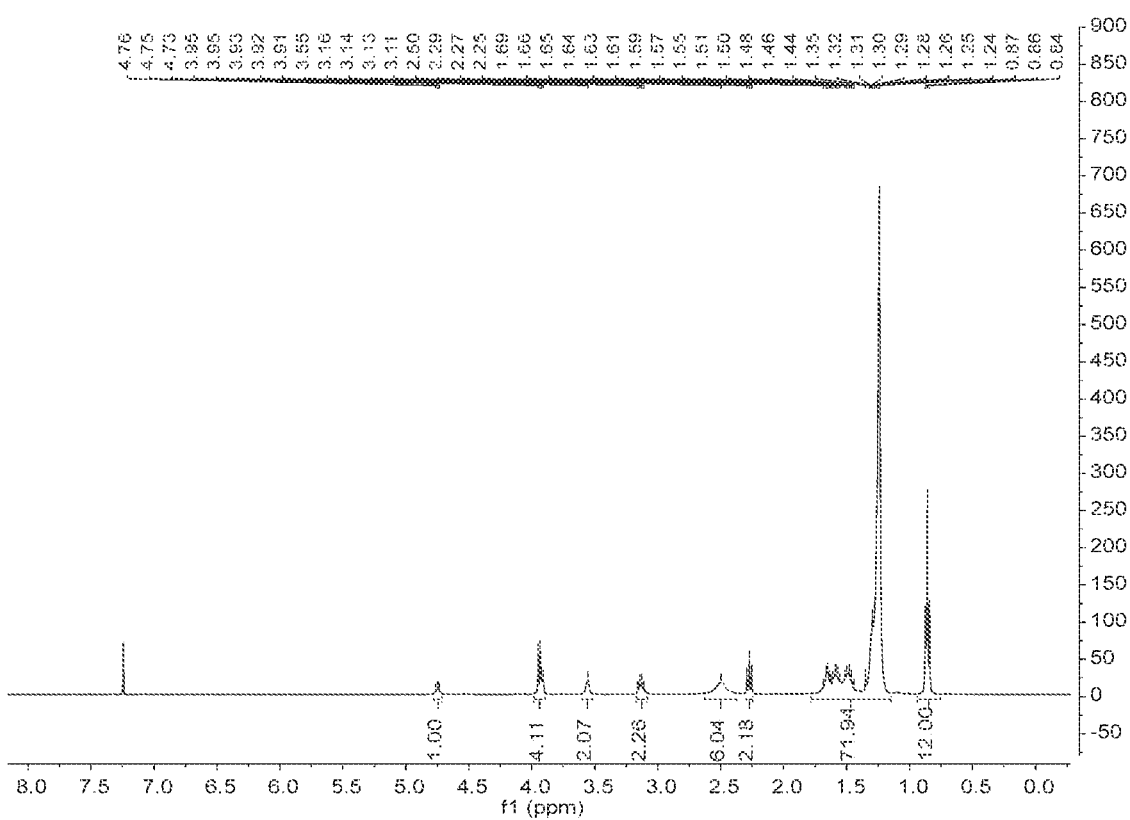
FIG. 1 depicts the hydrogen spectrum of the E-1 lipid compound described in the present invention.

Nucleic acids, collectively referring to deoxyribonucleic acid (DNA) and ribonucleic acid (RNA), are biological macromolecules composed of multiple nucleotide monomers. Nucleic acids consist of nucleotides, each containing a pentose, a phosphate group, a nitrogenous base, or any modification group. If the pentose is ribose, the resulting polymer is RNA; if the pentose is deoxyribose, the resulting polymer is DNA.

Nucleic acid molecules include single-stranded DNA, double-stranded DNA, short isoforms, mRNA, tRNA, rRNA, long non-coding RNA (lncRNA), micro non-coding RNA (miRNA), siRNA, telomerase RNA component, small nuclear RNA (snRNA), circular RNA (circRNA), synthetic miRNA (miRNA mimics, miRNA agomir, miRNA antagomir), antisense DNA, antisense RNA, ribozymes, asymmetric interfering RNA (aiRNA), dicer-substrate RNA (dsRNA), small hairpin RNA (shRNA), gRNA, sgRNA, crRNA, tracrRNA, locked nucleic acid (LNA), peptide nucleic acid (PNA), morpholine antisense oligonucleotide, morpholine oligonucleotide, or biologically customized oligonucleotide. The examples provided here are not exhaustive, and any nucleotide polymer can be applied to the present invention.

When describing "C1-C20 linear or branched alkyl", it refers to an alkyl group with 1-20 carbon atoms (such as 1, 2, 3, 4, 5, 6, 7, 8, 9, 10, 11, 12, 13, 14, 15, 16, 17, 18, 19 or 20 carbon atoms), which is saturated and may be linear or branched. Any alkyl group meeting the aforementioned number of carbon atoms falls within the scope described by this term.

When describing "C2-C20 linear or branched alkenyl", it refers to an alkenyl group with 2-20 carbon atoms (such as 2, 3, 4, 5, 6, 7, 8, 9, 10, 11, 12, 13, 14, 15, 16, 17, 18, 19 or 20 carbon atoms), which may be linear or branched. Any alkenyl group that meets the aforementioned number of carbon atoms falls within the scope described by this term. In various embodiments described in present invention, the alkenyl group may be a monoolefin or a polyolefin (such as a dienefin).

When describing "C1-C10 alkylene", it refers to an alkylene group with 1-10 carbon atoms (such as 1, 2, 3, 4, 5, 6, 7, 8, 9 or 10 carbon atoms), which may be linear or branched.

The definition "carbamate bond" refers to —NH(C=O)O— or —O(C=O)NH—.

The definition "carbamate bond-containing lipid compound" refers to the presence of —NH(C=O)O— or —O(C=O)NH— on the hydrophobic group of the lipid compound.

The pharmaceutically acceptable salts include both acid and base addition salts.

Wherein the acids used in acid addition salts include, but are not limited to: hydrochloric acid, hydrobromic acid, sulfuric acid, nitric acid, phosphoric acid, acid phosphate, acetic acid, 2,2-dichloroacetic acid, adipic acid, alginic acid, ascorbic acid, aspartic acid, benzenesulfonic acid, benzoic acid, 4-acetylaminobenzoic acid, camphoric acid, camphor- 10-sulfonic acid, capric acid, hexanoic acid, caprylic acid, carbonic acid, cinnamic acid, citric acid, cyclic amino acid, dodecyl sulfuric acid, ethane-1,2-disulfonic acid, ethanesulfonic acid, 2-hydroxyethanesulfonic acid, formic acid, fumaric acid, galactolic acid, gentian acid, gluproheptanoic acid, gluconic acid, glucan acid, glucuronic acid, glutamic acid, glutaric acid, 2-oxoglutaric acid, glycerophosphate, glycolic acid, hippuric acid, isobutyric acid, lactic acid, lactobionic acid, lauric acid, maleic acid, malic acid, malonic acid, mandelic acid, methanesulfonic acid, mucoic acid, naphthalene-1,5-dicarboxylic acid, naphthalene-2-sulfonic acid, 1-hydroxy-2-naphthalic acid, niacin, oleic acid, orotic acid, oxalic acid, palmitic acid, palmitic acid, propionic acid, pyroglutamic acid, pyruvate, salicylic acid, 4-aminosalicylic acid, sebacic acid, stearic acid, succinic acid, tartaric acid, thiocyanic acid, p-toluenesulfonic acid, trifluoroacetic acid, quaternary ammonium acid, and undecylenic acid.

Examples of alkali metal salts include, but are not limited to: sodium salts, potassium salts, lithium salts, ammonium salts, calcium salts, magnesium salts, iron salts, zinc salts, copper salts, manganese salts, and aluminum salts; organic alkali include, but not limited to: ammonia, isopropylamine, trimethylamine, diethylamine, triethylamine, tripropylamine, diethanolamine, ethanolamine, dealcoholization, 2-dimethylaminoethanol, 2-diethylaminoethanol, lysine, arginine, histidine, caffeine, procaine, hydrazine, choline, betaine, benzamine, benzathine, ethylenediamine, glucosamine, methylglucosamine, theobromine, triethanolamine, purine, piperazine, piperidine, N-ethylpiperidine, and polyamine resins; preferably, the organic alkali are isopropylamine, diethylamine, ethanolamine, trimethylamine, dicyclohexylamine, choline, and caffeine.

The helper lipids include: phosphatidylcholine, phosphatidylethanolamine, sphingomyelin (SM), sterols and their derivatives, ceramides, and combinations of one or more charged lipids; preferred phosphatidylcholines include: DSPC, DPPC, DMPC, DOPC, POPC; DOPE is a preferred phosphatidylethanolamine; cholesterol is a preferred sterol; as an embodiment, charged lipids such as DOTAP, DOTMA, or 18PA can be used. The examples are not exhaustive, any combination of lipid compounds using the structure described in present invention falls within protection scope and is disclosed by the present invention. The examples are not exhaustive, and the selection of helper lipids is unrestricted. As long as the lipid compounds utilize the structure described in present invention, they fall within the protection scope and disclosed by this invention.

The charged lipids refer to a class of lipid compounds existing in the form of positive or negative charges. These charges are independent on the physiological pH (such as pH 3-9) range, and are unaffected by pH. Charged lipids can be synthetic or natural origin. Examples of charged lipids include, but are not limited to, DOTAP, DOTMA, and 18PA.

mRNA, also referred to as messenger RNA, is a single-stranded ribonucleic acid transcribed from a strand of DNA, carrying genetic information to guide protein synthesis. mRNA can be either monocistronic mRNA or polycistronic mRNA. Additionally, mRNA may contain one or more functional nucleotide analogues, such as pseudouracil, 1-methyl-pseudouracil, or 5-methylcytosine. The examples are not exhaustive, and any modified mRNA or its derivatives can be applied to the present invention.

The small molecule compounds can serve as active ingredients in reagents used for treatment or prevention, including anti-tumor drugs, anti-infectives, local anesthetics, antidepressants, anticonvulsants, antibiotics/antimicrobials, antifungals, antiparasitic drugs, hormones, hormone antagonists, immunomodulators, neurotransmitter antagonists, antiglaucoma agents, anesthetics, and imaging agents. The examples are not exhaustive.

The peptides are compounds formed by the linking of α-amino acids via peptide bonds, and they represent intermediate products of proteolysis.

The proteins are substances composed of amino acids linked together through "dehydration condensation" to form polypeptide chains that fold into specific spatial structures. Proteins can include interferons, protein hormones, cytokines, chemokines, and enzymes, etc.

The diluents are any water-soluble excipients known to those skilled in the art in this field, which can be pharmaceutically acceptable, including amino acids, monosaccharides, disaccharides, trisaccharides, tetrasaccharides, pentaccharides, other oligosaccharides, mannitol, dextroside, sodium chloride, sorbitol, polyethylene glycol, phosphates, or derivatives thereof.

The stabilizers can be any pharmaceutical excipients known to those skilled in the art in this field, including: Tween-80, sodium dodecyl sulfate, sodium oleate, mannitol, mannose, or sodium alginate, etc.

The preservatives can be any pharmaceutical preservatives known to those skilled in the art in this field, such as thimerosal, etc.

The lyoprotectants can be any pharmaceutical lyoprotectants known to those skilled in the art in this field, such as glucose, mannitol, sucrose, lactose, trehalose, or maltose, etc.

DSPC: Distearoyl Phosphatidylcholine, 1,2-distearoyl-sn-glycero-3-phospho-choline, CAS number: 816-94-4.

DPPC:1,2-dipalmitoyl-sn-glycero-3-phosphocholine, CAS number: 63-89-8.

DMPC:1,2-dimyristoyl-sn-glycero-3-phosphocholine, CAS number: 18194-24-6.

DOPC:1,2-dioleoyl-sn-glycero-3-phosphocholine, CAS number: 4235-95-4.

POPC:2-oleoyl-1-palmitoyl-sn-glycero-3-phosphocholine, CAS number: 26853-31-6.

DOPE:1,2-dioleoyl-sn-glycero-3-phosphoethanolamine, CAS number: 4004-05-1.

DOTAP:1,2-dioleoyl-3-trimethylammonium-propane (chloride salt), CAS number: 132172-61-3; the chemical structure formula is as follows:

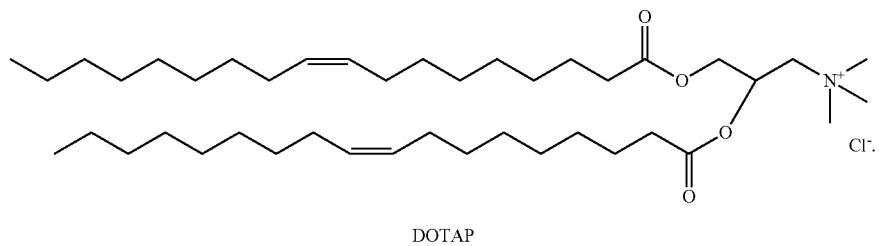

DOTAP

DOTMA: CAS number: 1325214-86-5, the chemical formula is as follows:

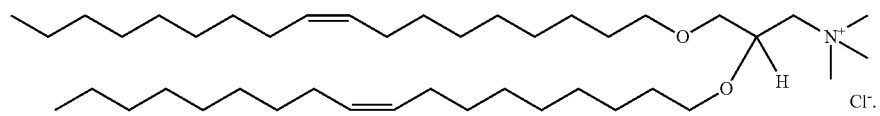

18PA: CAS number: 108392-02-5, the chemical structure formula is as follows:

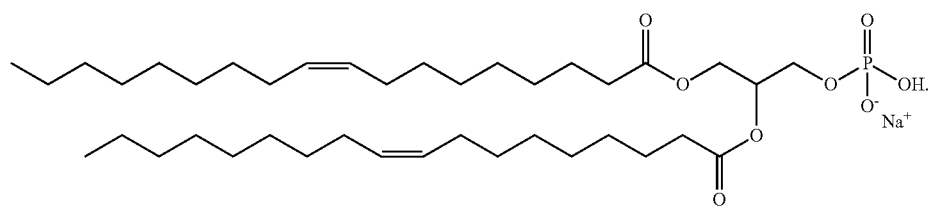

18PA

SM: sphingomyelin.

PEG: polyethylene glycol.

Amphiphilic block copolymers refer to copolymers containing segments of PEG and one or more polymer components selected from the following: polylactic acid-polyglycolic acid copolymer (PLGA), polylactic acid (PLA), polycaprolactone (PCL), poly-original acid ester, polyanhydride, and poly$\beta$-amino ester (PBAE).

DETAILED DESCRIPTION

The present invention is introduced in detail with the drawings and examples.

The carbamate bond-containing lipid compounds are prepared by the preparation described in Example 1.

Example 1

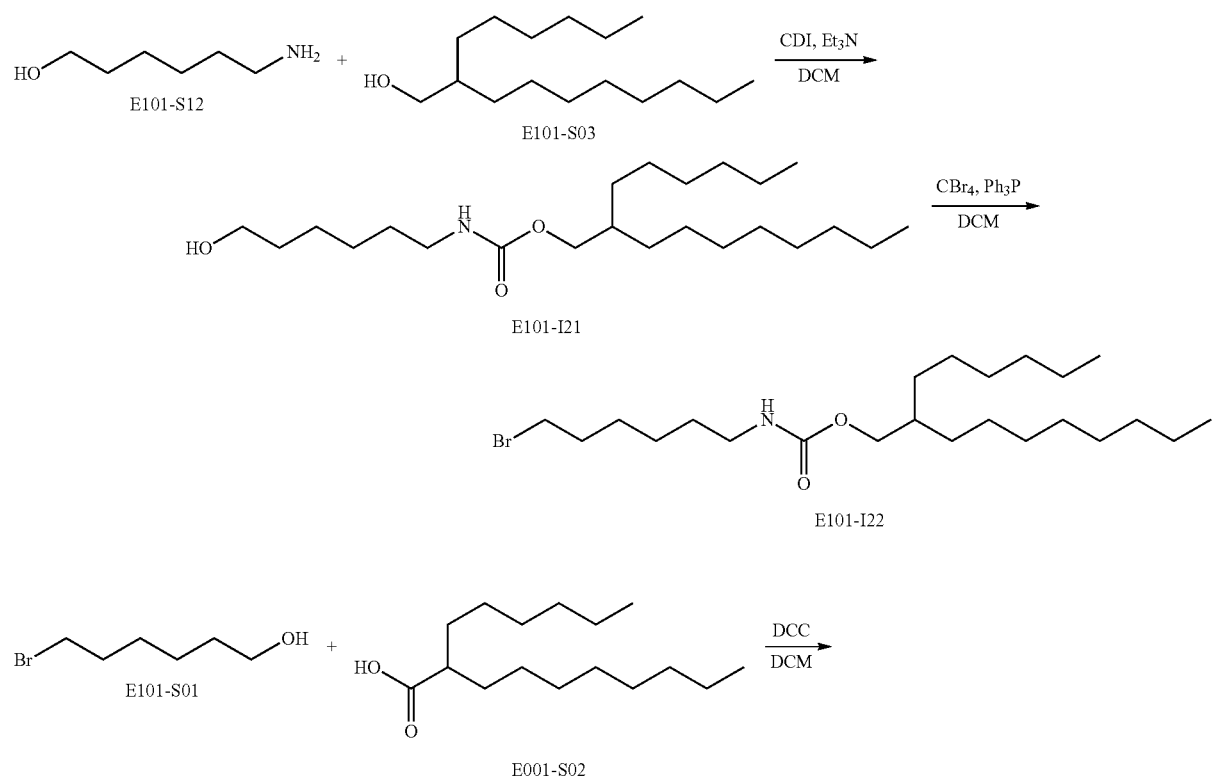

-continued

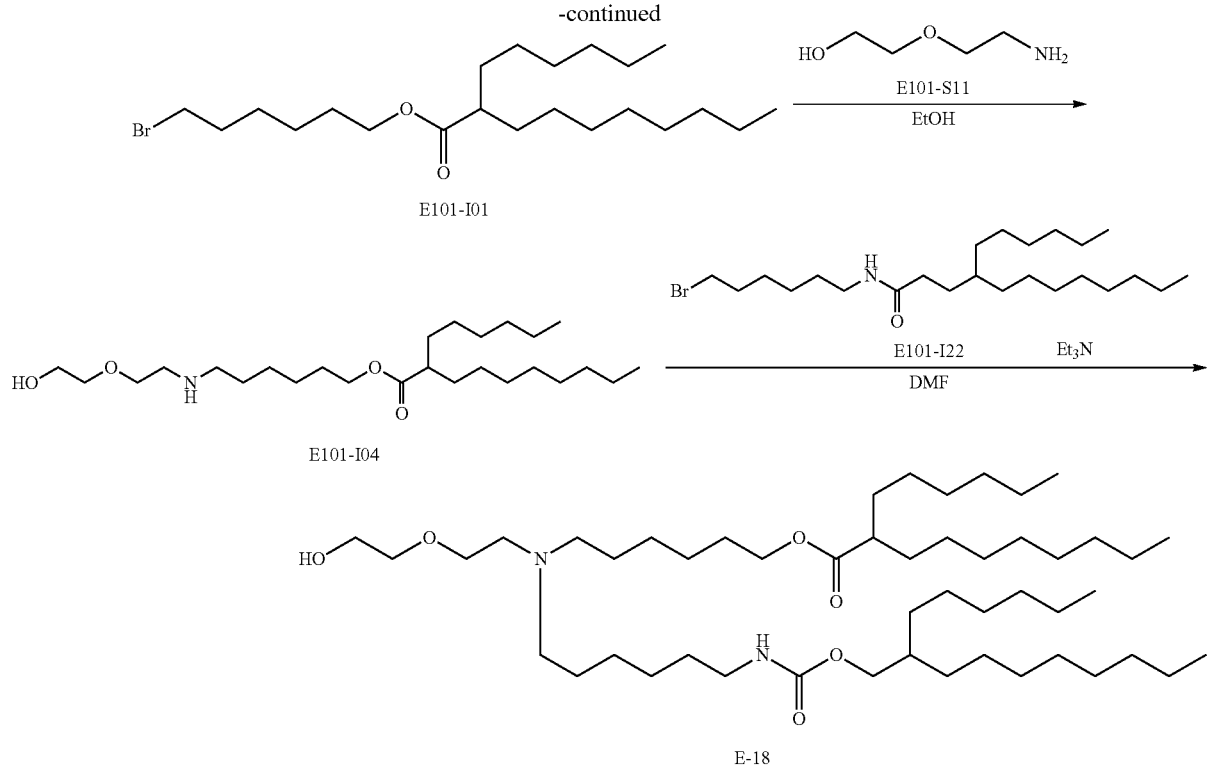

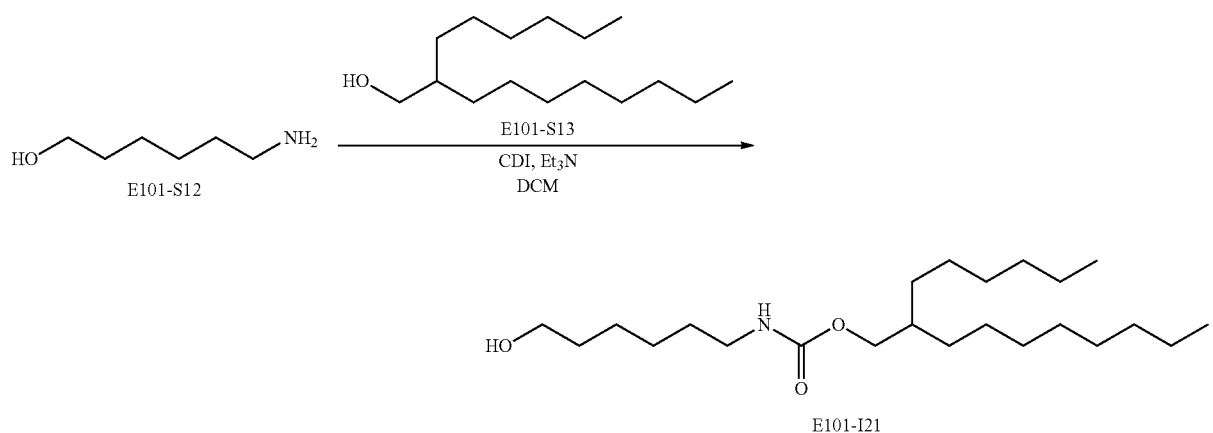

Synthesis of compound E101-I21. E101-S13 (4.84 g, 20.0 mmol) dissolved in DCM (20 mL), Et$_3$N (3.9 mL) and CDI (3.24 g, 20 mmol) were added to the solution and stirred for 1.5 h at 50° C. Then E101-S12 (3.52 g, 30.0 mmol) was added and stirred at 50° C. for 2h. After cooled to room temperature, the reaction mixture was washed with 5% citric acid solution (20 mL×2) and saturated saline (10 mL) successively, the organic phase was dried by anhydrous sodium sulfate, and concentrated to obtain the crude product. The crude product was purified by column chromatography (DCM:EtOH=100:1) to obtain 6.88 g of the product, yield: 89.1%.

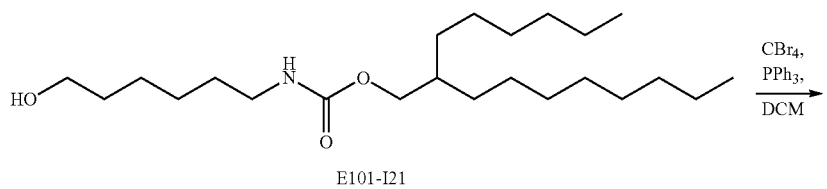

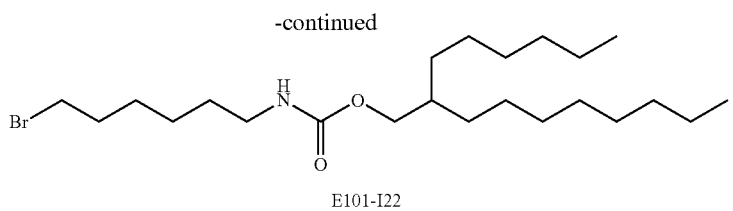

E101-I22

Synthesis of compound E101-I22. E101-I21 (6.88 g, 17.84 mmol) was dissolved in DCM (54 mL), then PPh$_3$ (7.02 g, 26.76 mmol) was added. CBr$_4$ (8.87 g, 26.76 mmol, 1.5 eq) was added in batches and reacted for 25 min in an ice bath. The reaction was quenched by 10 mL methanol, and directly concentrated to obtain the crude product. The crude product was purified by column chromatography (PE:EA=10:1) to obtain 7.52 g of the product yield: 94.0%.

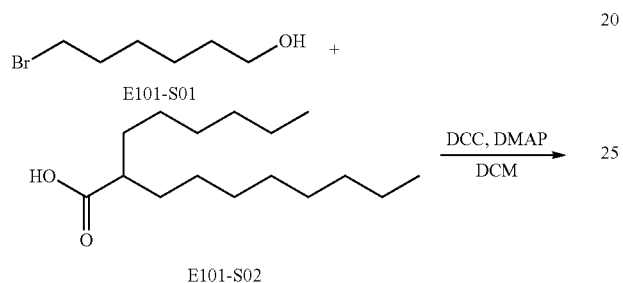

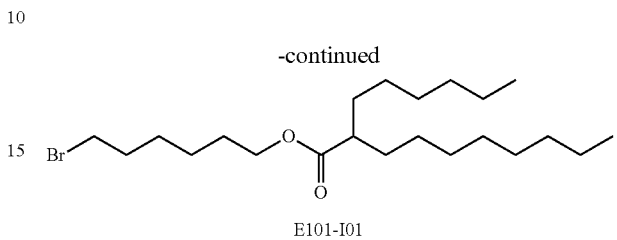

E101-I01

Synthesis of compound E101-I01. E101-S01 (3.62 g, 20 mmol), E101-S02 (5.12 g, 20 mmol) and DMAP (0.85 g, 7 mmol) were dissolved in DCM (60 mL), cooled to 0° C. and DCC (4.32 g, 21 mmol) was added, heated to room temperature and stirred overnight. The reaction solution was filtered, concentrated, then separated and purified by column (silica gel column, the eluent was PE:EA=50:1) to obtain 8.0 g of the product, yield: 89%.

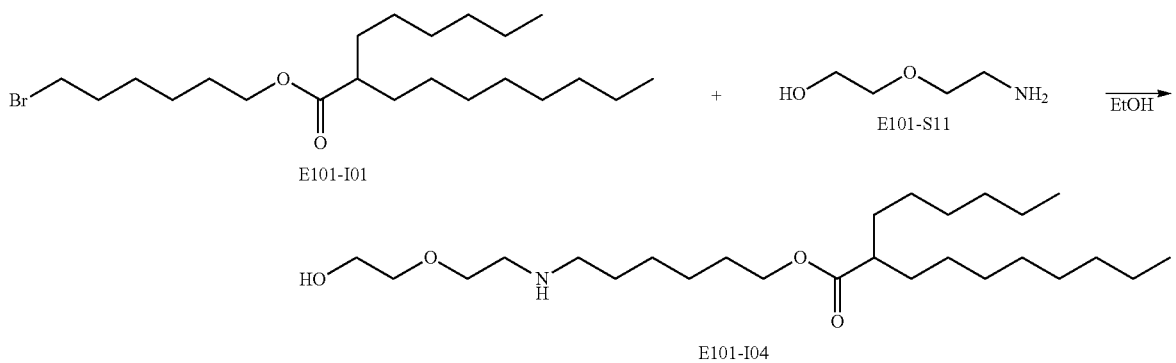

E101-I04

Synthesis of compound E101-I04. E101-I01 (2.25 g, 5.0 mmol), E101-S11 (5.26 g, 50.0 mmol) and EtOH (3.0 mL) were added to heavy-wall pressure vessel, heated to 90° C. and reacted overnight. The reaction solution was concentrated, and poured into ethyl acetate/water (1:1) ethyl ester for extraction. Then the organic phase was washed once with water and twice with saturated saline. The organic phase was concentrated to obtain 2.26 g of the product, yield: 100%.

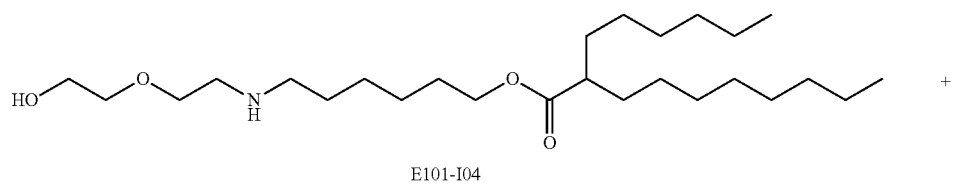

E101-I04

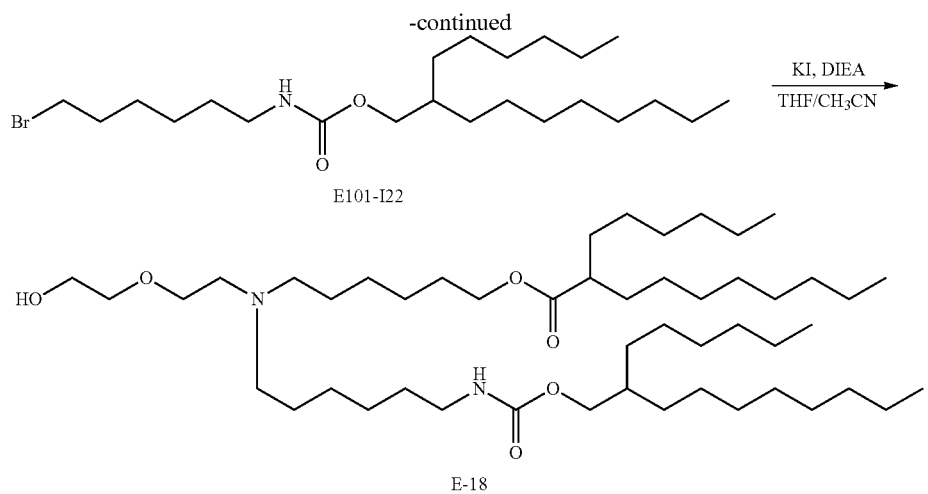

Synthesis of compound E-18. E101-I04 (300 mg, 0.676 mmol), E101-I22 (364 mg, 0.811 mmol), DIEA (222 µL, 1.27 mmol), KI (34 mg, 0.2 mmol), THF (1.0 mL), and CH₃CN (1.0 mL) were added to heavy-wall pressure vessel, heated to 80° C. and reacted overnight. The reaction solution was concentrated, dissolved in ethyl acetate, washed once with saturated sodium bicarbonate solution/water (1:2), washed once with saturated saline, dried and concentrated in organic phase, then separated and purified by column (silica gel column, eluent is 1.5-3% MeOH in DCM+0.5% NH₃H₂O) to obtain 343 mg of the product, yield: 63%. MS m/z(ESI):811.7[M+H]⁺.

The method of Example 1 can also be used to prepare compounds E-1~E-17, E-18~E-21, E-25, and E-27 by substitution of corresponding starting materials, which will not be repeated here.

Example 2

Compound synthesis route:

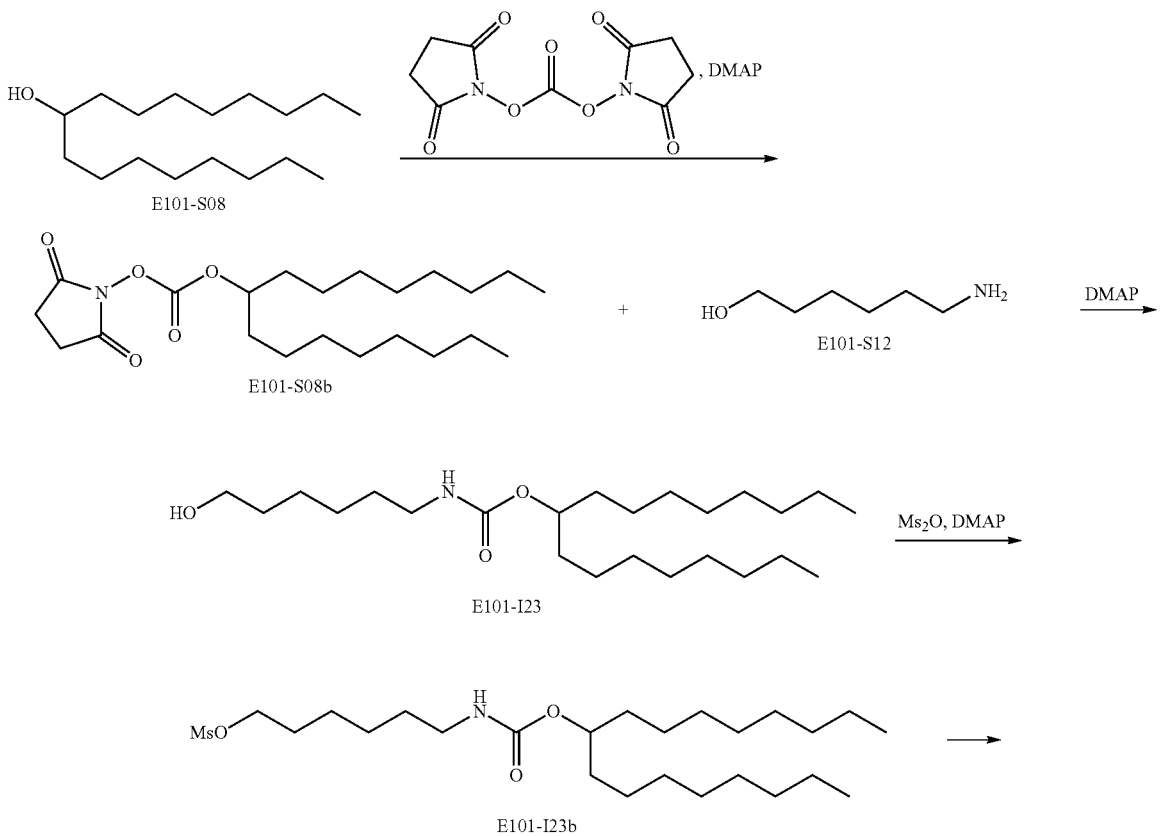

-continued

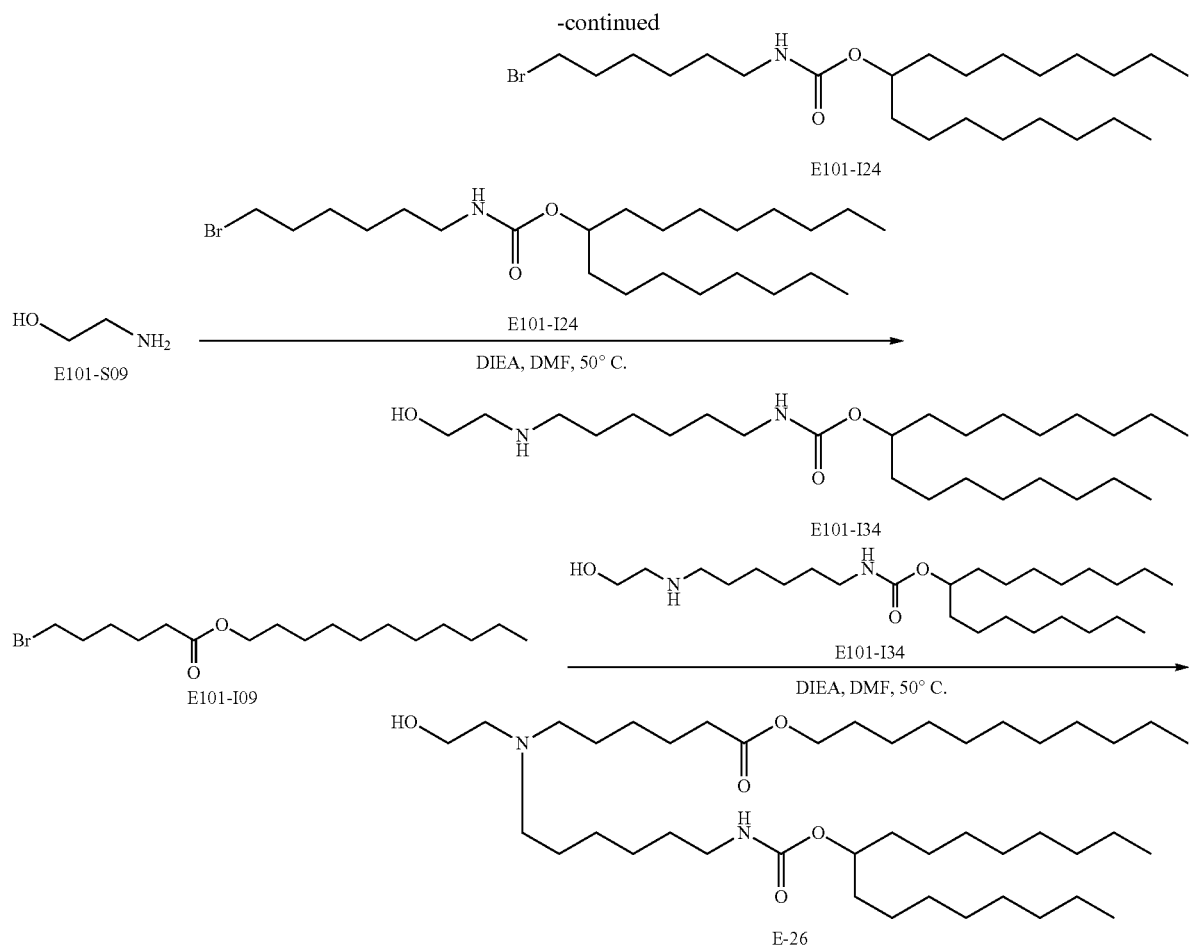

Specific methods for compound synthesis:

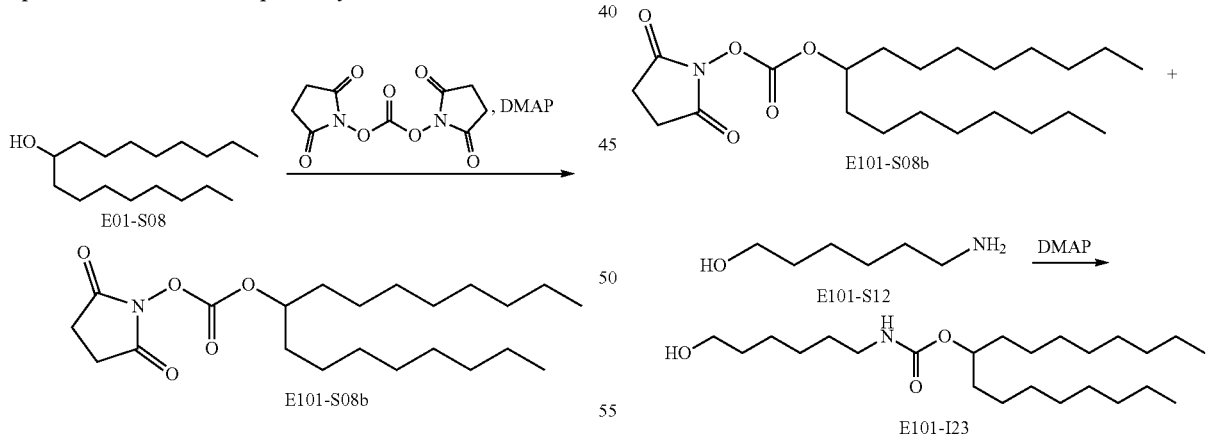

Synthesis of compound E101-S08b. E101-S08 (3.85 g, 15 mmol), N,N'-disuccinimidyl carbonate (5.84 g, 22.8 mmol), and DMAP (2.75 g, 22.5 mmol) were added to DMF (60 mL), heated to 75° C., and stirred overnight. The reaction solution was poured into 300 mL water, and extracted twice with ethyl acetate. The organic phase was mixed and washed three times with saturated saline. The organic phase was dried and concentrated, and purified by silica gel column chromatography (silica gel column, the eluent was PE:EA=50:1) to obtain 1.8 g of the product, yield: 42%.

Synthesis of compound E101-I23. E101-S08b (1.8 g, 4.53 mmol), F101-S12 (636 mg, 5.43 mmol), and DMAP (554 mg, 4.53 mmol) were added to DMF (30 mL), heated to 60° C., and stirred overnight. The reaction solution was poured into 300 mL water, and extracted twice with ethyl acetate. The organic phase was mixed and washed three times with saturated saline. The organic phase was dried and concentrated to obtain 1.84 g of the product with a yield of 100%, which can be directly used in the next step of the reaction.

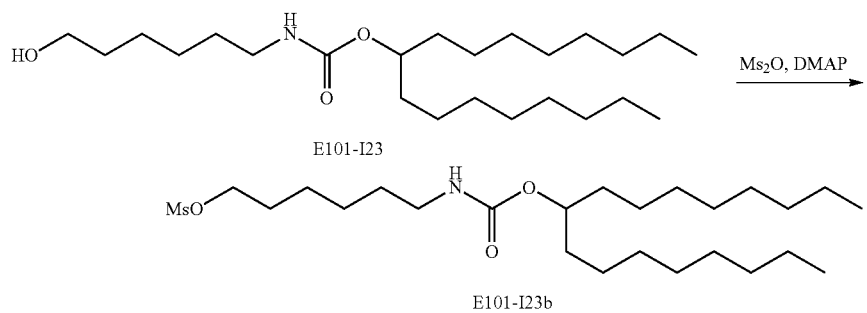

Synthesis of compound E101-I23b. E101-I23 (1.84 g, 4.53 mmol), DMAP (61 mg, 0.5 mmol), and TEA (2.5 mL, 18 mmol) were dissolved in DCM (60 mL), and Ms$_2$O (1.57 g, 9 mmol) in DCM was slowly added to the solution at 0° C. The solution was stirred at 0° C. for 30 min, then the reaction was quenched with water (100 mL). The organic phases was separated, washed once with water, once with 10% citric acid, and once with saturated saline. The organic phase was dried and concentrated to obtain 2.05 g of the crude product, which can be directly used in the next step of the reaction.

Synthesis of compound E101-I24. E101-I23b (2.05 g, 4.29 mmol) and LiBr (1.2 g, 13.6 mmol) were added to THF (25 mL), heated to 45° C., and stirred overnight. and the solution was filtered by the silica gel. The filtrate was concentrated, and purified by the silica gel column chromatography (silica gel column, the eluent was PE:EA=10:1), to obtain 1.84 g of the product, yield: 93%.

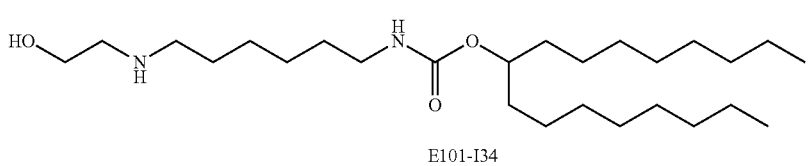

Synthesis of compound E101-I34. E101-S09 (310.0 mg, 5.07 mmol, 3 eq) was dissolved in DMF (3.4 mL), E101-I24 (782.5 mg, 1.69 mmol, 1 eq) and DIEA (655.9 mg, 5.07 mmol, 3 eq) were added to react at 50° C. for 18 h. The reaction mixture was cooled to room temperature, then ethyl acetate (40 mL) was added. The organic phase was washed with semi-saturated saline (5 mL×3) and saturated saline successively, dried with anhydrous sodium sulfate, and concentrated to obtain a crude product. The crude product was purified by column chromatography (DCM:EtOH=20:1) to obtain 364.3 mg of light yellow oil product. Yield: 48.7%.

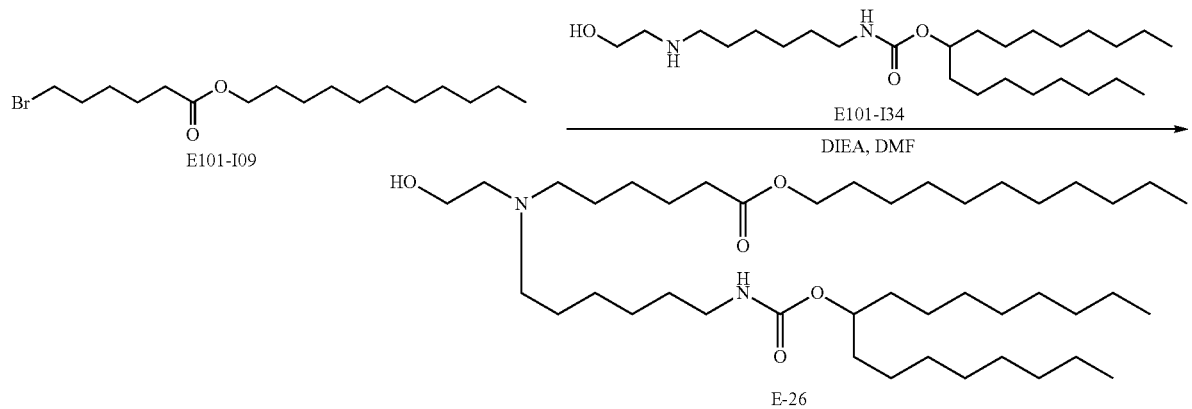

Synthesis of compound E-26. E101-I34 (364.3 mg, 822.85 μmol, 1 eq) was dissolved in DMF (1.0 mL), DIEA (319.1 mg, 2.47 mmol, 3 eq) and E101-I09 (431.2 mg, 1.23 mmol, 1.5 eq) were added to react at 50° C. for 16 h. The reaction mixture was cooled to room temperature, ethyl acetate (40 mL) was added, the organic phase was washed by semi-saturated saline (5 mL×3) and saturated saline successively, dried with anhydrous sodium sulfate, and concentrated to obtain the crude product. The crude product was purified by column chromatography (DCM:EtOH=100:1, 50:1, 20:1, 13:1) to obtain 335.7 mg light yellow oil product. Yield: 57.4%. MS m/z (ESI):711.7[M+H]$^+$.

Example 3

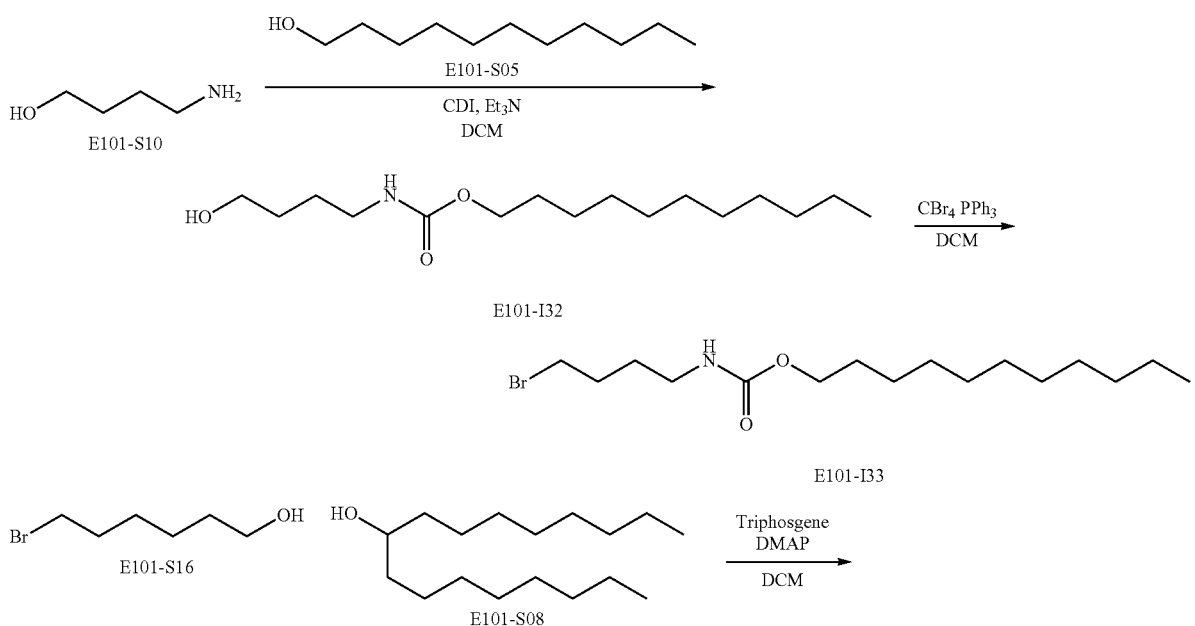

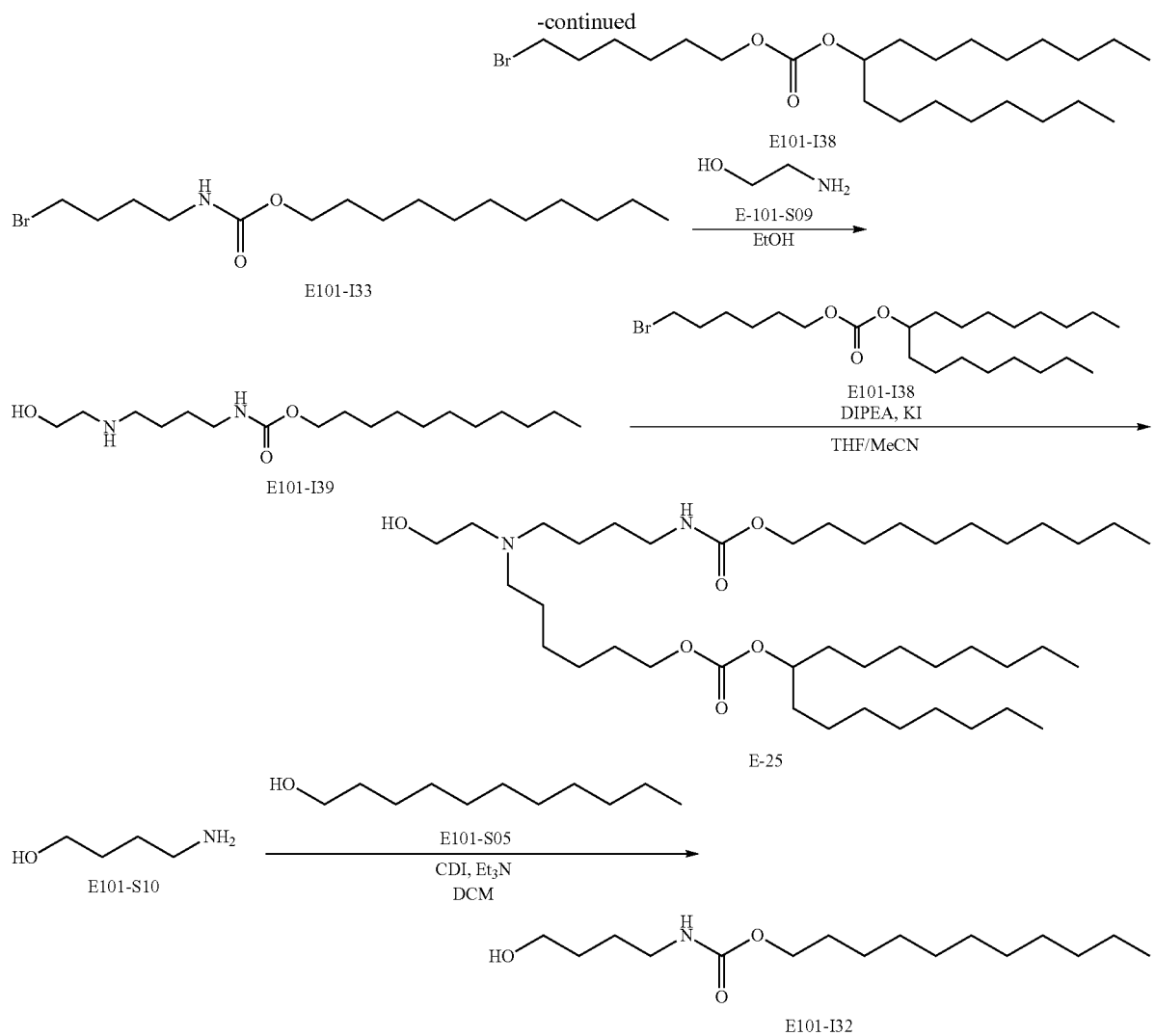

Synthesis of compound E101-I32. E101-S05 (3.45 g, 20.0 mmol, 1 eq) was dissolved in DCM (20 mL). Et₃N (3.9 mL) and CDI (3.24 g, 20 mmol, 1 eq) were added to the solution to react for 1.5 h at 50° C. E101-S10 (2.67 g, 30.0 mmol, 1.5 eq) was then added and reacted at 50° C. for 16 h. The reaction mixture was cooled to room temperature, washed with 5% citric acid (20 mL×2) and saturated saline (10 mL) successively. The organic phase was dried by anhydrous sodium sulfate, filtered and concentrated to obtain a crude product. DCM (20 mL) was added to the crude product, stirred for 10 min, suction filtrated. The filter cake was washed with a small amount of DCM, and concentrated to obtain 3.77 g of the product. Yield: 65%.

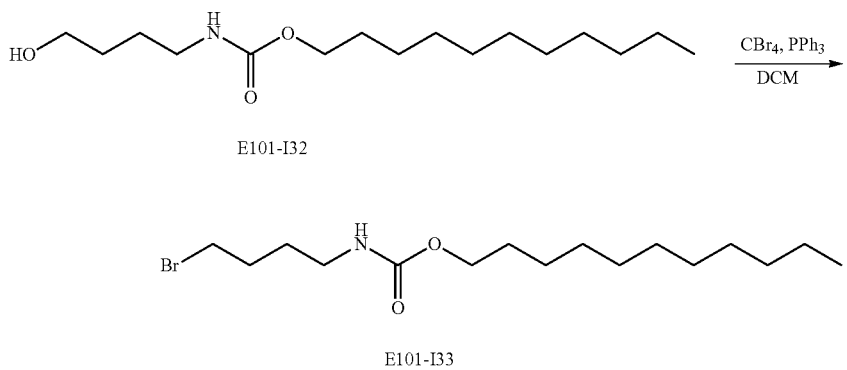 [SMILES: CCCCCCCCCCCOC(=O)NCCCCO ; CCCCCCCCCCCOC(=O)NCCCCBr]

Synthesis of compound E101-I33. E101-I32 (3.77 g, 13.12 mmol, 1 eq) was dissolved in DCM (39 mL), PPh$_3$ (5.16 g, 19.67 mmol, 1.5 eq) was added, CBr$_4$ (6.52 g, 19.67 mmol, 1.5 eq) was added in batches and reacted in an ice bath for 20 min. The mixture was quenched with 10 mL of methanol was added to quench the reaction, and the crude product was obtained by direct concentration. The crude product was purified by column chromatography (PE:EA=10:1) to obtain 2.70 g of the product, yield: 58.8%.

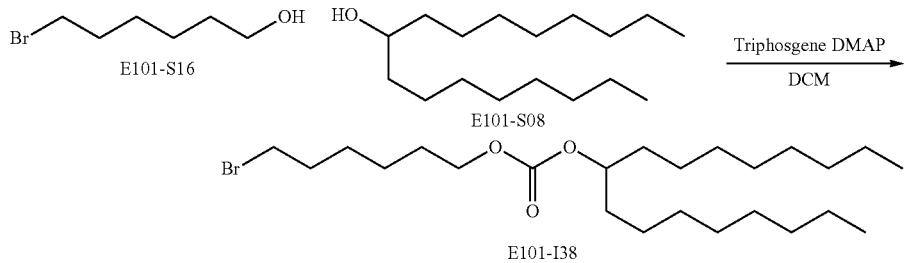

Synthesis of compound E101-I38. Triphosgene (1.01 g, 3.41 mmol, 0.35 eq) was dissolved in DCM (50 mL), DMAP dissolved in 50 mL DCM (4.17 g, 33.12 mmol, 3.5 eq) was added dropwise under ice bath condition. After dropwise addition, the solution was stirred under ice bath condition for 10 minutes. E101-S08 (1.01 g, 3.41 mmol, 0.35 eq) was added dropwise, then warmed to room temperature gradually, and stirred for further 2 hours. E101-S16 was added dropwise under ice bath conditions, then gradually returned to room temperature, and stirred for further 2 hours. The reaction solution was washed with saturated sodium bicarbonate solution (100 mL×2) and saturated saline (100 mL×1) successively, dried by anhydrous sodium sulfate, and concentrated to obtain a crude product. The crude product was filtered and purified by silica gel, and 4 g of crude product is obtained after concentration, which can be directly used for the next step of the reaction.

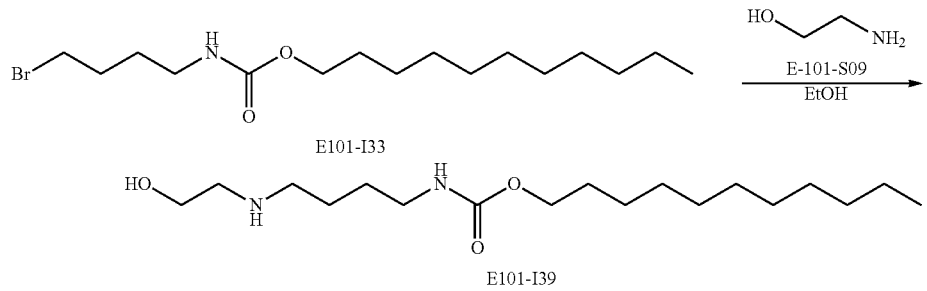

Synthesis of compound E101-I39. E101-I33 (1.0 g, 2.85 mmol, 1.0 eq), E101-S09 (1.74 g, 28.54 mmol, 10.0 eq) were dissolved in ethanol (5 mL), heated at 88° C. in sealed-tube to react for 12 hours. After cooled to room temperature, 100 mL of ethyl acetate was added to the solution, washed with saturated sodium bicarbonate solution (100 mL×2) and saturated saline (100 mL×1) successively, dried with anhydrous sodium sulfate, and concentrated to obtain a crude product. The crude product was pulping purified by 20 mL of PE, and filtered to obtain 0.31 g of the product, yield: 33%.

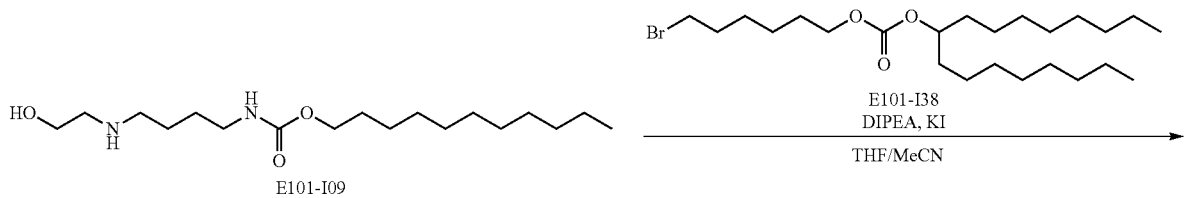

-continued

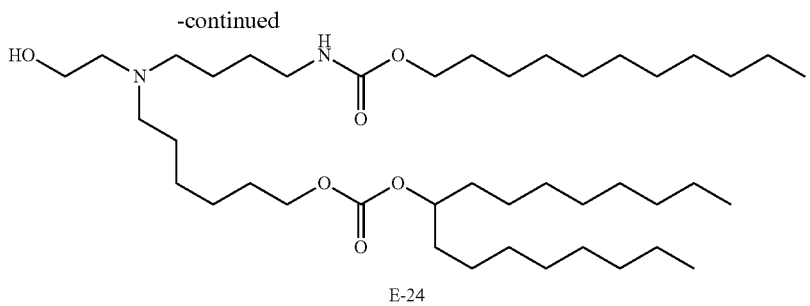

E-24

Synthesis of compound E-24. E101-I39 (0.30 g, 0.91 mmol, 1 eq), F101-I38 (0.63 g, 1.36 mmol, 1.5 eq), DIPEA (0.15 g, 1.18 mmol, 1.3 eq), and KI (15 mg, 0.09 mmol, 0.1 eq) were dissolved in THF/MeCN (2.0 mL+2.0 mL), and reacted in a sealed-tube at 86° C. for 12 h. The mixture was cooled to room temperature, and ethyl acetate (100 mL) was added. The organic phase was washed with saturated sodium bicarbonate solution (100 mL×2) and saturated saline (100 mL×1) successively, dried with anhydrous sodium sulfate, and concentrated to obtain a crude product. The crude product was separated and purified by column (DCM: EtOH=50:1) to obtain 0.24 g of light yellow oily product, and the yield was 37.1%. MS m/z (ESI): 713.7 [M+H]$^+$. E-22, E-23 can be obtained by the method of Example 3, by replacing the corresponding starting materials.

Example 4

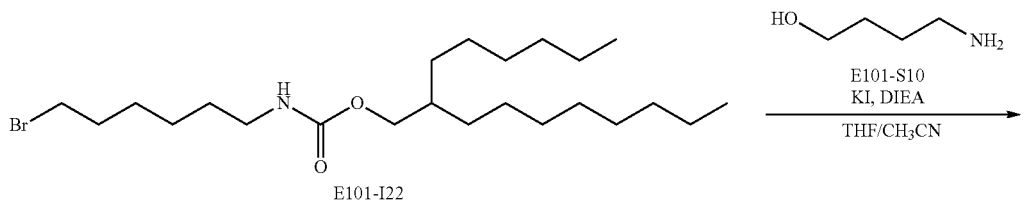

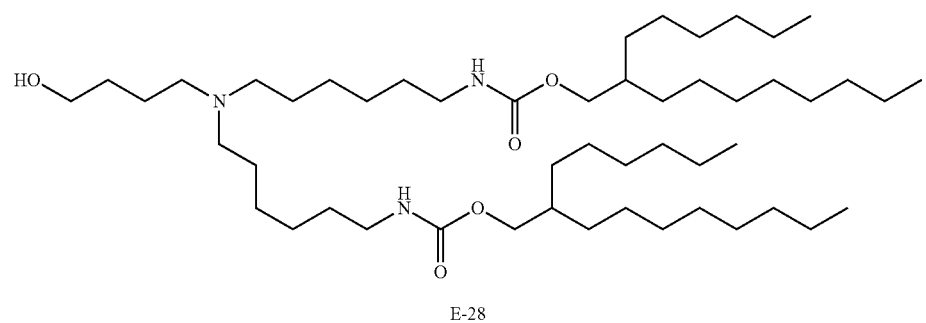

E-28

Synthesis of compound E-28. E101-I22 (500 mg, 1.11 mmol), E101-S10 (40.0 mg, 0.45 mmol), DIEA (173 mg, 1.34 mmol), KI (14 mg, 0.09 mmol), THF (1.0 mL), and CH$_3$CN (1.0 mL) were added to heavy-wall pressure vessel and heated to 80° C. to react overnight. The reaction solution was concentrated, dissolved in ethyl acetate, washed once with saturated sodium bicarbonate solution/water (1:2), once with saturated saline. The organic phase was dried and concentrated, and purified by column separation (silica gel column, eluent is 1.5-3% MeOH in DCM) to obtain 260 mg of light yellow oil product, yield: 71%. MS m/z (ESI): 824.5[M+H]$^+$.

The H-NMR data for the compounds are shown below and in FIG. 1:

| Compound | H¹ NMR |
|---|---|
| E-1 | ¹H NMR (400 MHz, Chloroform-d) δ 4.79-4.70 (m, 1H), 3.98-3.89 (m, 4H), 3.55 (s, 2H), 3.13 (q, J = 6.8 Hz, 2H), 2.50 (s, 6H), 2.27 (t, J = 7.5 Hz, 2H), 1.78-1.15 (m, 72H), 0.86 (t, J = 6.6 Hz, 12H). |
| E-2 | ¹H NMR (400 MHz, Chloroform-d) δ 4.65 (s, 1H), 3.93 (dd, J = 9.0, 5.7 Hz, 4H), 3.62 (s, 2H), 3.14 (q, J = 6.8 Hz, 2H), 2.75-2.50 (m, 6H), 2.28 (t, J = 7.5 Hz, 2H), 1.65-1.18 (m, 68H), 0.86 (t, J = 6.6 Hz, 12H). |
| E-3 | ¹H NMR (400 MHz, Chloroform-d) δ 4.74 (t, J = 6.0 Hz, 1H), 4.03 (t, J = 6.6 Hz, 2H), 3.92 (d, J = 5.8 Hz, 2H), 3.55 (s, 2H), 3.14 (q, J = 6.8 Hz, 2H), 2.56-2.24 (m, 7H), 1.76-0.97 (m, 69H), 0.86 (td, J = 6.9, 2.2 Hz, 12H). |
| E-4 | ¹H NMR (400 MHz, Chloroform-d) δ 4.65 (s, 1H), 4.46 (s, 1H), 4.04 (t, J = 6.6 Hz, 2H), 3.92 (d, J = 5.8 Hz, 2H), 3.56 (t, J = 5.3 Hz, 2H), 3.14 (q, J = 6.8 Hz, 2H), 2.62 (s, 2H), 2.49 (s, 4H), 2.29 (tt, J = 9.2, 5.2 Hz, 1H), 1.72-1.10 (m, 65H), 0.86 (td, J = 6.7, 2.0 Hz, 12H). |
| E-5 | ¹H NMR (400 MHz, Chloroform-d) δ 4.74-4.63 (m, 2H), 4.04 (t, J = 6.6 Hz, 2H), 3.55 (s, 2H), 3.13 (q, J = 6.8 Hz, 2H), 2.54-2.25 (m, 7H), 1.72-1.14 (m, 72H), 0.85 (t, J = 6.6 Hz, 12H). |
| E-6 | ¹H NMR (400 MHz, Chloroform-d) δ 4.75 (s, 1H), 4.52 (s, 1H), 4.03 (t, J = 6.6 Hz, 2H), 3.92 (d, J = 5.8 Hz, 2H), 3.55 (s, 2H), 3.14 (q, J = 6.8 Hz, 2H), 2.48 (s, 6H), 2.28 (tt, J = 9.2, 5.3 Hz, 1H), 1.76-1.14 (m, 6H), 0.85 (dd, J = 7.5, 5.6 Hz, 12H). |
| E-7 | ¹H NMR (400 MHz, Chloroform-d) δ 4.67 (s, 1H), 4.39 (s, 1H), 4.02 (dt, J = 9.4, 6.6 Hz, 4H), 3.54 (s, 2H), 3.08 (t, J = 6.0 Hz, 2H), 2.51-2.23 (m, 7H), 1.73-1.10 (m, 69H), 0.86 (td, J = 6.9, 2.3 Hz, 12H). |
| E-8 | ¹H NMR (400 MHz, Chloroform-d) δ 4.65 (s, 1H), 4.47 (s, 1H), 3.93 (dd, J = 9.7, 5.6 Hz, 4H), 3.56 (s, 2H), 3.14 (q, J = 6.8 Hz, 2H), 2.62 (s, 2H), 2.50 (s, 4H), 2.29 (t, J = 7.4 Hz, 2H), 1.70-1.18 (m, 64H), 0.86 (t, J = 6.6 Hz, 12H). |
| E-9 | ¹H NMR (400 MHz, Chloroform-d) δ 4.75 (s, 1H), 3.93 (dd, J = 9.9, 5.7 Hz, 4H), 3.54 (s, 2H), 3.13 (q, J = 6.9 Hz, 2H), 2.44 (s, 6H), 2.29 (t, J = 7.5 Hz, 2H), 1.71-1.18 (m, 68H), 0.86 (t, J = 6.6 Hz, 12H). |
| E-10 | ¹H NMR (400 MHz, Chloroform-d) δ 4.68 (q, J = 6.4 Hz, 2H), 4.47 (s, 1H), 3.94 (d, J = 5.8 Hz, 2H), 3.54 (s, 2H), 3.13 (q, J = 6.7 Hz, 2H), 2.46 (s, 6H), 2.29 (t, J = 7.4 Hz, 2H), 1.70-1.15 (m, 59H), 0.85 (dt, J = 7.0, 3.3 Hz, 12H). |
| E-11 | ¹H NMR (400 MHz, Chloroform-d) δ 4.68 (q, J = 6.1 Hz, 1H), 4.40 (s, 1H), 4.01 (t, J = 6.6 Hz, 2H), 3.94 (d, J = 5.8 Hz, 2H), 3.55 (s, 2H), 3.08 (t, J = 6.0 Hz, 2H), 2.48 (s, 6H), 2.27 (t, J = 7.5 Hz, 2H), 1.72-1.18 (m, 72H), 0.86 (t, J = 6.7 Hz, 12H). |
| E-12 | ¹H NMR (400 MHz, Chloroform-d) δ 4.65 (s, 1H), 4.46 (s, 1H), 3.94 (dd, J = 8.5, 5.7 Hz, 4H), 3.55 (s, 2H), 3.14 (q, J = 6.7 Hz, 2H), 2.61 (s, 2H), 2.48 (s, 4H), 2.28(t, J = 7.5 Hz, 2H), 1.67-1.13 (m, 52H), 0.86 (dq, J = 6.9, 3.8, 3.0 Hz, 12H). |
| E-13 | ¹H NMR (400 MHz, Chloroform-d) δ 4.76-4.67 (m, 1H), 4.59 (s, 1H), 3.95 (d, J = 5.8 Hz, 2H), 3.60 (s, 2H), 3.14 (q, J = 6.7 Hz, 2H), 2.73-2.42 (m, 6H), 2.28(t, J = 7.5 Hz, 2H), 1.68-1.12 (m, 51H), 0.86 (td, J = 6.8, 2.5 Hz, 12H). |
| E-14 | ¹H NMR (400 MHz, Chloroform-d) δ 4.73-4.61 (m, 2H), 3.94 (d, J = 5.8 Hz, 2H), 3.71 (t, J = 5.6 Hz, 2H), 3.17-3.05 (m, 4H), 2.97 (t, J = 8.2 Hz, 4H), 2.28 (t, J = 7.4 Hz, 2H), 1.94 (p, J = 7.0 Hz, 2H), 1.79 (s, 4H), 1.70-1.43 (m, 13H), 1.40-1.19 (m, 36H), 0.86 (td, J = 6.8, 2.3 Hz, 12H). |
| E-15 | ¹H NMR (400 MHz, Chloroform-d) δ 4.69 (s, 1H), 4.54 (s, 1H), 3.93 (dd, J = 9.0, 5.7 Hz, 4H), 3.73-3.57 (m, 6H), 3.14 (dd, J = 13.1, 6.4 Hz, 2H), 2.73-2.42 (m, 6H), 2.27 (t, J = 7.5 Hz, 2H), 1.69-1.40 (m, 12H), 1.38-1.18 (m, 56H), 0.86 (t, J = 6.6 Hz, 12H). |
| E-16 | ¹H NMR (400 MHz, Chloroform-d) δ 4.69 (s, 1H), 4.51(s, 1H), 4.09 (t, J = 6.7 Hz, 2H), 4.01 (d, J = 5.8 Hz, 2H), 3.92 (d, J = 5.8 Hz, 2H), 3.75-3.57 (m, 6H), 3.14 (q, J = 6.8 Hz, 2H), 2.76-2.37 (m, 6H), 1.70-1.17 (m, 66H), 0.86 (t, J = 6.7 Hz, 12H). |
| E-17 | ¹H NMR (400 MHz, Chloroform-d) δ 4.69 (s, 1H), 4.48 (s, 1H), 3.93 (dd, J = 9.6, 5.7 Hz, 4H), 3.72-3.56 (m, 6H), 3.14 (q, J = 6.8 Hz, 2H), 2.74-2.42 (m, 6H), 2.29 (t, J = 7.4 Hz, 2H), 1.68-1.18 (m, 64H), 0.86 (t, J = 6.6 Hz, 12H). |
| E-18 | ¹H NMR (400 MHz, Chloroform-d) δ 4.69 (s, 1H), 4.52 (s, 1H), 4.03 (t, J = 6.6 Hz, 2H), 3.92 (d, J = 5.8 Hz, 2H), 3.69-3.56 (m, 6H), 3.13 (q, J = 6.8 Hz, 2H), 2.64 (s, 2H), 2.48 (s, 4H), 2.29 (td, J = 9.1, 4.7 Hz, 1H), 1.66-1.10 (m, 65H), 0.85 (td, J = 6.8, 2.0 Hz, 12H). |
| E-19 | ¹H NMR (400 MHz, Chloroform-d) δ 4.75-4.60 (m, 2H), 4.45 (s, 1H), 3.94 (d, J = 5.7 Hz, 2H), 3.70-3.56 (m, 6H), 3.13 (q, J = 6.7 Hz, 2H), 2.65 (s, 2H), 2.49 (s, 4H), 2.29 (t, J = 7.4 Hz, 2H), 1.68-1.19 (m, 55H), 0.86 (td, J = 6.8, 2.1 Hz, 12H). |
| E-20 | ¹H NMR (400 MHz, Chloroform-d) δ 4.72 (s, 1H), 3.93 (dd, J = 9.5, 5.8 4H), 3.79-3.68 (m, 4H), 3.61 (dd, J = 5.4, 3.2 Hz, 2H), 3.14 (q, J = 6.7 Hz, 2H), 2.99-2.65 (m, 6H), 2.28 (t, J = 7.4 Hz, 2H), 1.72-1.17 (m, 52H), 0.96-0.78 (m, 12H). |
| E-21 | ¹H NMR (400 MHz, Chloroform-d) δ 4.68 (q, J = 6.5 Hz, 2H), 3.94 (d, J = 5.8 Hz, 2H), 3.84-3.69 (m, 4H), 3.61 (dd, J = 5.2, 3.3 Hz, 2H), 3.13 (q, J = 6.7 Hz, 2H), 3.06-2.68 (m, 6H), 2.28 (t, J = 7.5 Hz, 2H), 1.78-1.13 (m, 51H), 0.86 (td, J = 6.8, 2.4 Hz, 12H). |
| E-22 | ¹H NMR (400 MHz, Chloroform-d) δ 4.74 (s, 1H), 4.66 (p, J = 6.3 Hz, 1H), 4.09 (t, J = 6.6 Hz, 2H), 3.92 (d, J = 5.8 Hz, 2H), 3.55(s, 2H), 3.13(q, J = 6.7 Hz, 2H), 2.48 (s, 6H), 1.64 (q, J = 7.6 Hz, 6H), 1.60-1.42 (m, 11H), 1.41-1.20 (m, 44H), 0.86 (t, J = 6.5 Hz, 12H). |
| E-23 | ¹H NMR (400 MHz, Chloroform-d) δ 4.75 (s, 1H), 4.52 (s, 1H), 4.09 (t, J = 6.7 Hz, 2H), 4.00 (d, J = 5.8 Hz, 2H), 3.92 (d, J = 5.8 Hz, 2H), 3.55 (s, 2H), 3.13 (q, J = 6.8 Hz, 2H), 2.47 (s, 6H), 1.71-1.19 (m, 70H), 0.86 (t, J = 6.6 Hz, 12H). |
| E-24 | ¹H NMR (400 MHz, Chloroform-d) δ 4.84 (t, J = 6.0 Hz, 1H), 4.66 (p, J = 6.2 Hz, 1H), 4.09 (t, J = 6.7 Hz, 2H), 4.01 (t, J = 6.8 Hz, 2H), 3.56 (t, J = 5.3 Hz, 2H), 3.15 (t, J = 6.6 Hz, 2H), 2.66-2.42 (m, 6H), 1.71-1.18 (m, 58H), 0.85 (t, J = 6.6 Hz, 9H). |
| E-25 | ¹H NMR (400 MHz, Chloroform-d) δ 5.66-5.54 (m, 1H), 5.53-5.46 (m, 1H), 4.77 (s, 1H), 4.58 (t, J = 6.7 Hz, 2H), 4.04 (t, J = 6.7 Hz, 2H), 3.54 (s, 2H), 3.14 (q, J = 6.7 Hz, 2H), 2.53-2.24 (m, 7H), 2.07 (q, J = 7.2 Hz, 2H), 1.72-1.13 (m, 52H), 0.86 (td, J = 6.9, 2.3 Hz, 9H). |
| E-26 | ¹H NMR (400 MHz, Chloroform-d) δ 4.75-4.63 (m, 1H), 4.63-4.55 (m, 1H), 4.03 (t, J = 6.7 Hz, 2H), 3.56 (s, 2H), 3.14 (q, J = 6.8 Hz, 2H), 2.62 (s, 2H), 2.50 (s, 4H), 2.28 (t, J = 7.4 Hz, 2H), 1.68-1.18 (m, 60H), 0.85 (t, J = 6.6 Hz, 9H). |
| E-27 | ¹H NMR (400 MHz, Chloroform-d) δ 4.84 (p, J = 6.2 Hz, 2H), 4.01 (t, J = 6.7 Hz, 2H), 3.58 (t, J = 5.0 Hz, 2H), 3.21-3.11 (m, 2H), 2.63 (s, 2H), 2.51 (s, 4H), 2.26 (t, J = 7.5 Hz, 2H), 1.69-1.13 (m, 60H), 0.86 (t, J = 6.6 Hz, 9H). |
| E-28 | ¹H NMR (400 MHz, Chloroform-d) δ 4.77 (p, J = 6.0 Hz, 2H), 4.59 (s, 1H), 3.91 (d, J = 5.8 Hz, 4H), 3.54 (t, J = 4.6 Hz, 2H), 3.12 (q, J = 6.7 Hz, 4H), 2.55-2.41 (m, 6H), 1.70-1.61 (m, 4H), 1.59-1.41 (m, 10H), 1.36-1.16 (m, 56H), 0.92-0.79 (m, 12H). |

As an application, the aforementioned compounds can be used to prepare compositions for pharmaceutical use, including: carriers, loaded drugs, and pharmaceutical adjuvants. Carriers comprise one or more lipids compounds containing carbamate bonds, helper lipids, structural lipids, polymer-conjugated lipids, or amphiphilic block copolymers.

As an embodiment, the carriers are LNPs with an average size ranging from 30-200 nm, and the polydispersity index of the nanoparticle formulation is ≤0.3. It should be noted that any nanoparticles prepared using the lipid compounds described in this invention fall within the scope of this patent and are disclosed by this invention. For instance, aside from LNPs, they may also be one or more doped nanoparticles formed by lipid compounds and polymers containing carbamate bonds, such as PLGA-PEG, PLA-PEG, PCL, PBAE (Poly β-amino acid), etc. The examples are not exhaustive.

The helper 1 include: phosphatidylcholine, phosphatidylethanolamine, sphingomyelin (SM), sterols and their derivatives, ceramides, and combinations of one or more charged lipids: preferred phosphatidylcholines include: DSPC, DPPC, DMPC, DOPC, POPC; DOPE is a preferred phosphatidylethanolamine: cholesterol is a preferred sterol: as an embodiment, charged lipids such as DOTAP, DOTMA, or 18PA can be used. The examples are not exhaustive, any combination of lipid compounds using the structure described in present invention falls within protection scope and is disclosed by the present invention. The examples are not exhaustive, and the selection of helper lipids is unrestricted. As long as the lipid compounds utilize the structure described in present invention, they fall within the protection scope and disclosed by this invention.

The structural lipids include one or more cholesterols, nonsterols, sitosterols, ergosterols, campesterols, stigmasterols, brassisterols, tomatines, tomatines, ursolic acids, α-tocopherols, or corticosteroids. The examples are not exhaustive, and the selection of structural lipids is not restricted. Any lipid compounds with the structure listed in this invention fall within the scope of protection of this invention and are disclosed by this invention.

The polymer-conjugated lipids are pegylated lipids: as an embodiment, the pegylated lipids include one or more PEG-modified phosphatidylethanolamines, PEG-modified phosphatidic acids, PEG-modified ceramides, PEG-modified dialkylamines, PEG-modified diacylglycerols, or PEG-modified dialkylglycerols. The examples are not exhaustive, and the selection of polymer-conjugated lipids is not limited. Any lipid compounds with the structure listed in the present invention fall within the scope of protection described in present invention and are disclosed by this invention.

As an embodiment, an amphiphilic block copolymer may comprise amphiphilic block copolymers modified with polylactic acid-polyglycolic acid (PLGA), polylactic acid (PLA), polycaprolactones (PCL), polyprisates, polyanhydrides, poly(β-aminoesters) (PBAE), polyethylene glycol (PEG)-modified amphiphilic block copolymers, or the combination thereof. It should be noted that the examples here are not exhaustive, any lipid compounds with the structure listed in the present invention fall within the scope of protection described in present invention The loaded drugs include one or more nucleic acid molecules, small molecule compounds, peptides, or proteins. The examples are not exhaustive, as any lipid compounds with the structure listed in the present invention, regardless of the selected drug, they fall within the protective scope described in present invention and are disclosed by this invention.

The pharmaceutical adjuvants include one or more diluents, stabilizers, preservatives, or lyoprotectants. The examples are not exhaustive, as any lipid compounds with the structure listed in the present invention, regardless of the selected pharmaceutical adjuvants, they fall within the protective scope described in present invention and are disclosed by this invention.

Experiment 1: Preparation of mRNA-LNPs

The method for preparing mRNA-LNPs is as follows:

The lipid compounds (Lipid), DOPE (AVT (Shanghai) Pharmaceutical Tech Co., Ltd.), cholesterol (AVT (Shanghai) Pharmaceutical Tech Co., Ltd.), and PEG-lipid listed in Table 1 were dissolved in ethanol with a designed prescription ratio (Lipid/DOPE/cholesterol/lipid-PEG at 35/25/38.5/1.5 molar ratio) to prepare a lipid ethanol solution (with a lipid concentration of 20 mg/mL). The lipid compounds (ALC0315 and the other compounds listed in Table 1) corresponding to the commercially available positive control (Pfizer vaccine BNT162b2) were dissolved in ethanol at their optimized ratio (Lipid/DSPC/cholesterol/lipid-PEG at 46.3/9.4/42.7/1.6 molar ratio) to obtain a lipid ethanol solution (with a lipid concentration of 20 mg/mL).

Step 2: The mRNA was prepared at a mass ratio of LNPs to mRNA ranging from 10:1 to 30:1, and the mRNA was diluted to 0.2 mg/mL by citrate or sodium acetate buffer (pH=3 or 5).

Figure 2:
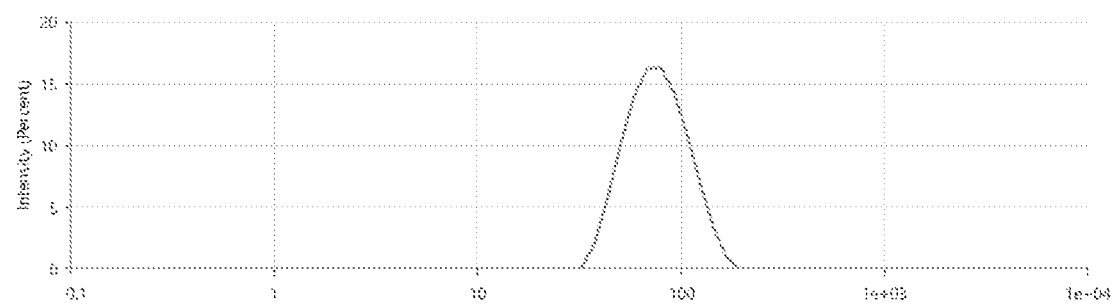
FIG. 2 depicts the particle size distribution diagram of the E-1 lipid compound described in the present invention.

Step 3: The lipid ethanol solution obtained in Step 1 was thoroughly mix with the mRNA solution at a volume ratio ranging from 1:5 to 1:1. The yielded nanoparticles were purified through ultrafiltration and dialysis, followed by filtration and sterilization. The average particle size and polydispersity index (PDI) of mRNA-LNPs (lipid nanoparticles encapsulating mRNA) were characterized using Malvern Zetasizer Nano ZS, and mRNA encapsulation efficiency was determined using Ribogreen RNA Quantification Assay Kit (Thermo Fisher). As shown in Table 1 and FIG. 2, the LNPs described in the present invention can form stable nanostructures with a narrow size distribution, with average size ranging from 60-120 nm depending on their chemical structures and nanostructures.

TABLE 1

| mRNA-LNP sample | Structure of lipid compound | Size (nm) | PDI (polydispersity index) | encapsulation efficiency (%) |
| --- | --- | --- | --- | --- |
| Commercially available comparison sample ALC-0315 | | 82.1 | 0.143 | 95.4 |
| Sample E-1 | | 72.1 | 0.092 | 98.7 |

TABLE 1-continued

| mRNA-LNP sample | Structure of lipid compound | Size (nm) | PDI (polydispersity index) | encapsulation efficiency (%) |
|---|---|---|---|---|
| Sample E-2 | | 82.3 | 0.103 | 96.5 |
| Sample E-3 | | 73.8 | 0.116 | 97.5 |
| Sample E-4 | | 81.9 | 0.076 | 95.4 |

TABLE 1-continued

| mRNA-LNP sample | Structure of lipid compound | Size (nm) | PDI (polydispersity index) | encapsulation efficiency (%) |
| --- | --- | --- | --- | --- |
| Sample E-5 | | 79.2 | 0.088 | 96.2 |
| Sample E-6 | | 81.5 | 0.075 | 95.8 |
| Sample E-7 | | 83.4 | 0.106 | 97.5 |

TABLE 1-continued

| mRNA-LNP sample | Structure of lipid compound | Size (nm) | PDI (polydispersity index) | encapsulation efficiency (%) |
|---|---|---|---|---|
| Sample E-8 | | 79.4 | 0.103 | 96.4 |
| Sample E-9 | | 83.8 | 0.096 | 96.2 |
| Sample E-10 | | 75.8 | 0.085 | 97.1 |

TABLE 1-continued

| mRNA-LNP sample | Structure of lipid compound | Size (nm) | PDI (polydispersity index) | encapsulation efficiency (%) |
| --- | --- | --- | --- | --- |
| Sample E-11 | | 74.7 | 0.074 | 95.8 |
| Sample E-12 | | 79.1 | 0.076 | 95.2 |
| Sample E-13 | | 84.5 | 0.089 | 97.5 |

TABLE 1-continued

| mRNA-LNP sample | Structure of lipid compound | Size (nm) | PDI (polydispersity index) | encapsulation efficiency (%) |
|---|---|---|---|---|
| Sample E-14 | | 75.2 | 0.106 | 96.1 |
| Sample E-15 | | 75.4 | 0.083 | 95.8 |
| Sample E-16 | | 82.7 | 0.085 | 95.2 |

TABLE 1-continued
| mRNA-LNP sample | Structure of lipid compound | Size (nm) | PDI (polydispersity index) | encapsulation efficiency (%) |
|---|---|---|---|---|
| Sample E-17 | 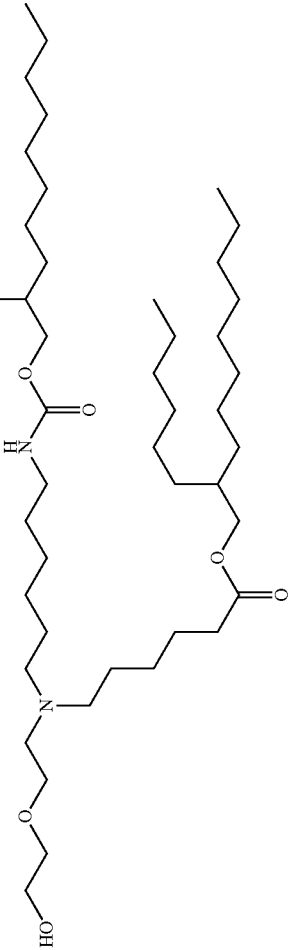 | 83.4 | 0.081 | 96.3 |
| Sample E-18 | 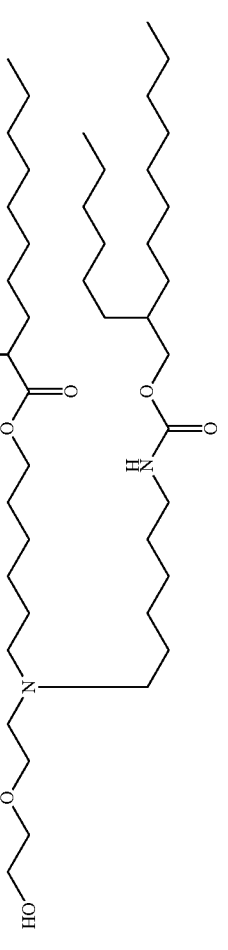 | 84.7 | 0.096 | 96.1 |
| Sample E-19 | 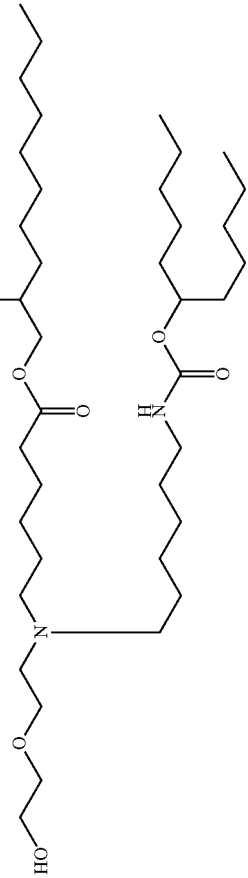 | 79.5 | 0.109 | 95.3 |

TABLE 1-continued

| mRNA-LNP sample | Structure of lipid compound | Size (nm) | PDI (polydispersity index) | encapsulation efficiency (%) |
|---|---|---|---|---|
| Sample E-20 | | 78.4 | 0.128 | 97.7 |
| Sample E-21 | | 81.4 | 0.121 | 95.9 |
| Sample E-22 | | 86.1 | 0.119 | 95.1 |

TABLE 1-continued

| mRNA-LNP sample | Structure of lipid compound | Size (nm) | PDI (polydispersity index) | encapsulation efficiency (%) |
|---|---|---|---|---|
| Sample E-23 | | 81.5 | 0.102 | 96.1 |
| Sample E-24 | | 79.5 | 0.115 | 95.8 |
| Sample E-25 | | 91.5 | 0.122 | 96.3 |

TABLE 1-continued

| mRNA-LNP sample | Structure of lipid compound | Size (nm) | PDI (polydispersity index) | encapsulation efficiency (%) |
|---|---|---|---|---|
| Sample E-26 | | 85.3 | 0.099 | 96.4 |
| Sample E-27 | | 88.2 | 0.089 | 97.1 |
| Sample E-28 | | 75.8 | 0.112 | 96.7 |

Experiment 2: Verification of Transfection Efficiency

Figure 3:
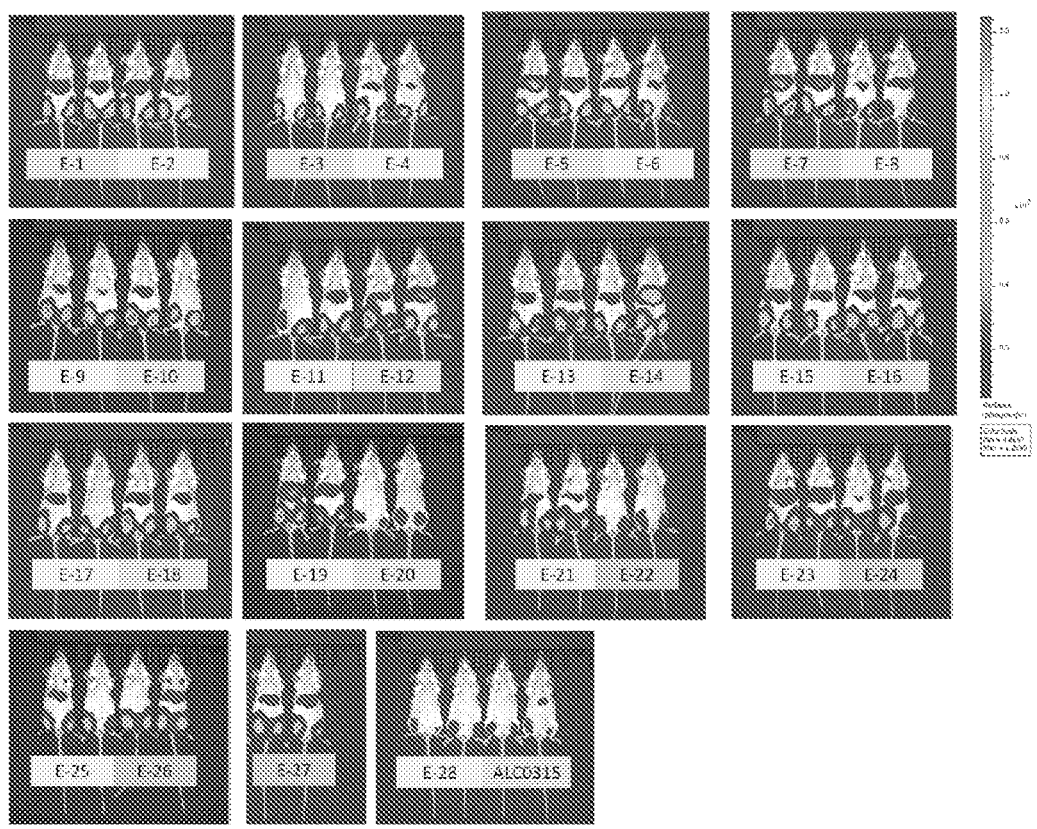
FIG. 3 depicts a fluorescence diagram of Luciferase mRNA transfected by LNP comprising compound E-1~E-28 and ALC0315 in Experiment 2 described in the present invention.

Male ICR mice (6-8 weeks old, Shanghai JieSiJie Laboratory Animal Co., Ltd.) were housed under experimental conditions with a temperature of 22±2° C. and relative humidity of 45-75%, with a light/dark cycle of 12 hours. The luciferase mRNA, encoding luciferase enzyme, was used as the reporter gene. Luciferase catalyzes fluorescein to produce biofluorescence, and the transfection efficiency of LNPs was determined by measuring the biofluorescence intensity per unit time. For example, luciferase mRNA (ApexBio Technology) and mRNA-LNP samples (E-1 to E-28 obtained in Experiment 1) along with the commercially available positive control sample ALC0315 were prepared; the aforementioned samples were administered by intramuscular injection at a dosage of 150 μg/kg mRNA into two legs of each mouse, two mice per sample group. At a specific time, each mouse received an intraperitoneally injection of fluorescein (20 μg/mL). After 5 minutes, the fluorescence intensity of each mouse were measured using a small animal in vivo imaging system, and the final results were expressed as the average fluorescence intensity. The experimental results of fluorescence intensity after intraperitoneal administration were shown in Table 2 and FIG. 3.

TABLE 2

| mRNA-LNP sample | Structure of lipid compound | Mean intensity (p/s/cm$^2$/sr) |
|---|---|---|
| Commercially available positive control sample ALC0315 | | 9.26E+06 |
| Sample E-1 | | 3.05E+08 |
| Sample E-2 | | 2.67E+08 |

TABLE 2-continued

| mRNA-LNP sample | Structure of lipid compound | Mean intensity (p/s/cm²/sr) |
|---|---|---|
| Sample E-3 | | 1.72E+08 |
| Sample E-4 | | 1.71E+08 |
| Sample E-5 | | 4.50E+08 |
| Sample E-6 | | 1.04E+08 |
| Sample E-7 | | 2.42E+08 |

TABLE 2-continued
| mRNA-LNP sample | Structure of lipid compound | Mean intensity (p/s/cm²/sr) |
|---|---|---|
| Sample E-8 | 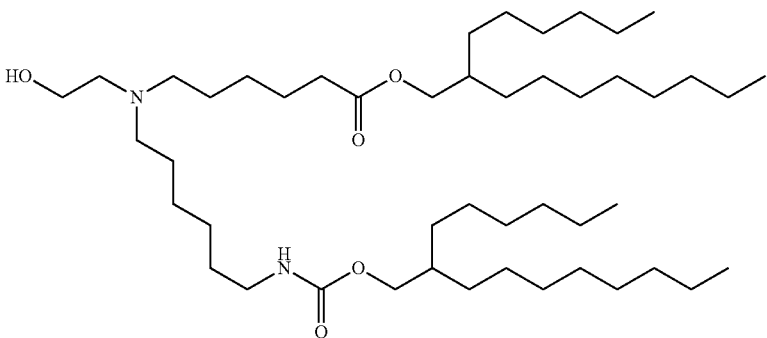 [SMILES: CCCCCCCCC(CCCCCC)COC(=O)CCCCCN(CCO)CCCCCCNC(=O)OCC(CCCCCC)CCCCCCCC] | 1.47E+08 |
| Sample E-9 | 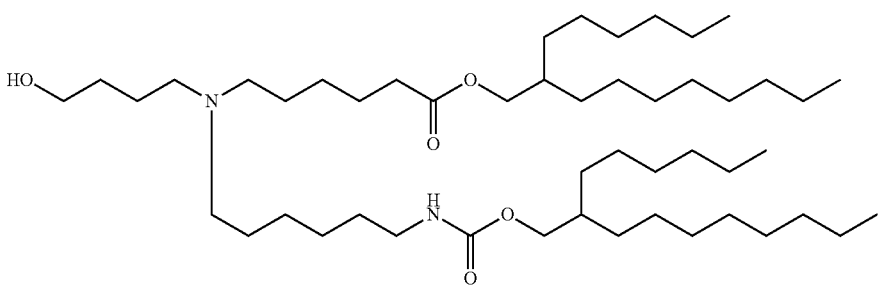 [SMILES: CCCCCCCCC(CCCCCC)COC(=O)CCCCCN(CCCCO)CCCCCCNC(=O)OCC(CCCCCC)CCCCCCCC] | 2.30E+08 |
| Sample E-10 | 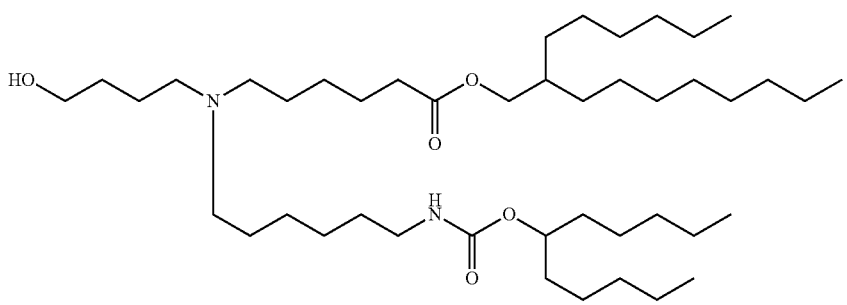 [SMILES: CCCCCCCCC(CCCCCC)COC(=O)CCCCCN(CCCCO)CCCCCCNC(=O)OC(CCCCC)CCCCC] | 3.59E+08 |
| Sample E-11 | 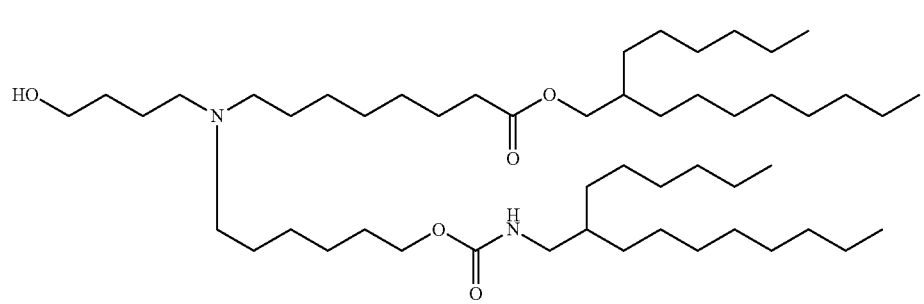 [SMILES: CCCCCCCCC(CCCCCC)CNC(=O)OCCCCCCN(CCCCO)CCCCCCCC(=O)OCC(CCCCCC)CCCCCCCC] | 1.92E+08 |
| Sample E-12 | 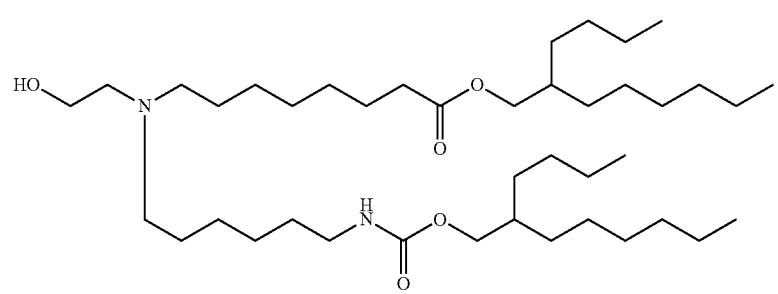 [SMILES: CCCCCCC(CCCC)COC(=O)CCCCCCCN(CCO)CCCCCCNC(=O)OCC(CCCC)CCCCCC] | 2.19E+08 |

TABLE 2-continued
| mRNA-LNP sample | Structure of lipid compound | Mean intensity (p/s/cm²/sr) |
|---|---|---|
| Sample E-13 | 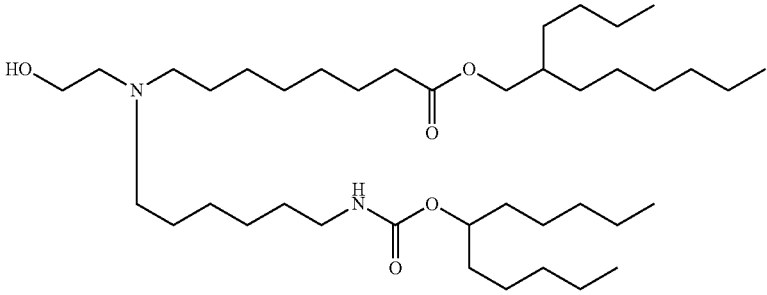 [SMILES: CCCCCCC(CCCC)COC(=O)CCCCCCCN(CCO)CCCCCCNC(=O)OC(CCCCC)CCCCC] | 2.98E+08 |
| Sample E-14 | 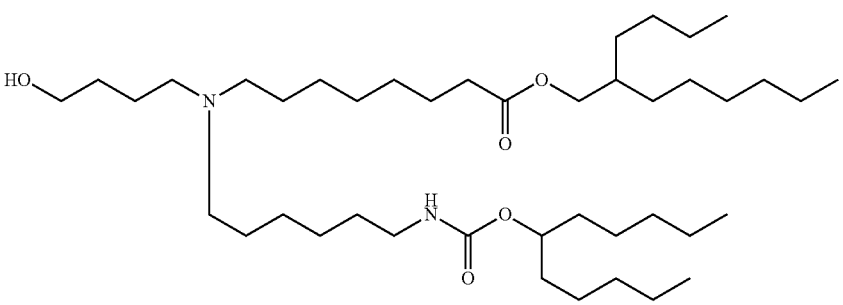 [SMILES: CCCCCCC(CCCC)COC(=O)CCCCCCCN(CCCCO)CCCCCCNC(=O)OC(CCCCC)CCCCC] | 2.35E+08 |
| Sample E-15 | 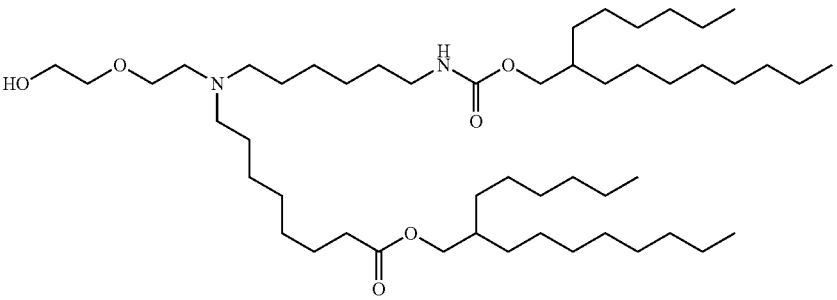 [SMILES: CCCCCCCCC(CCCCCC)COC(=O)CCCCCCCN(CCCCCCNC(=O)OCC(CCCCCC)CCCCCCCC)CCOCCO] | 1.93E+08 |
| Sample E-16 | 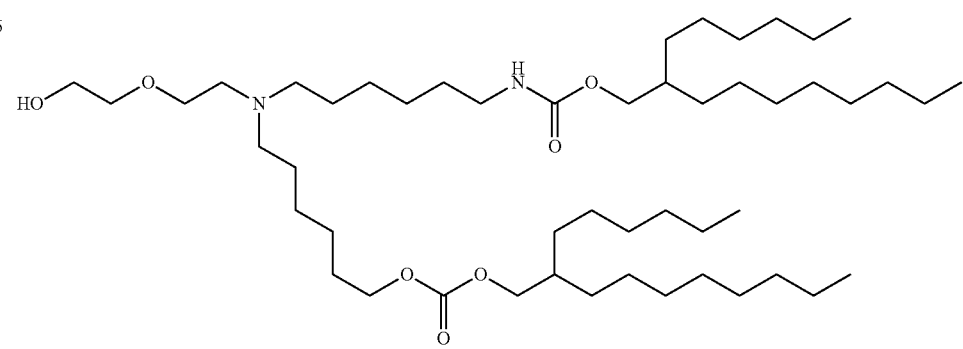 | 2.55E+08 |

TABLE 2-continued

| mRNA-LNP sample | Structure of lipid compound | Mean intensity (p/s/cm²/sr) |
|---|---|---|
| Sample E-17 | | 1.36E+08 |
| Sample E-18 | | 2.91E+08 |
| Sample E-19 | | 1.36E+08 |
| Sample E-20 | | 2.64E+07 |
| Sample E-21 | | 1.24E+08 |

TABLE 2-continued
| mRNA-LNP sample | Structure of lipid compound | Mean intensity (p/s/cm²/sr) |
|---|---|---|
| Sample E-22 | 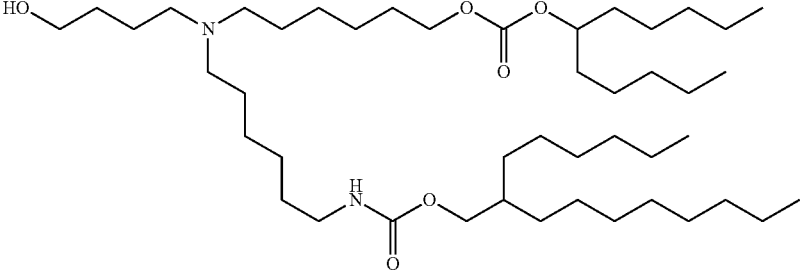 [SMILES: CCCCCCCCC(CCCCCC)COC(=O)NCCCCCCN(CCCCO)CCCCCCOC(=O)OC(CCCCC)CCCCC] | 2.56E+07 |
| Sample E-23 | 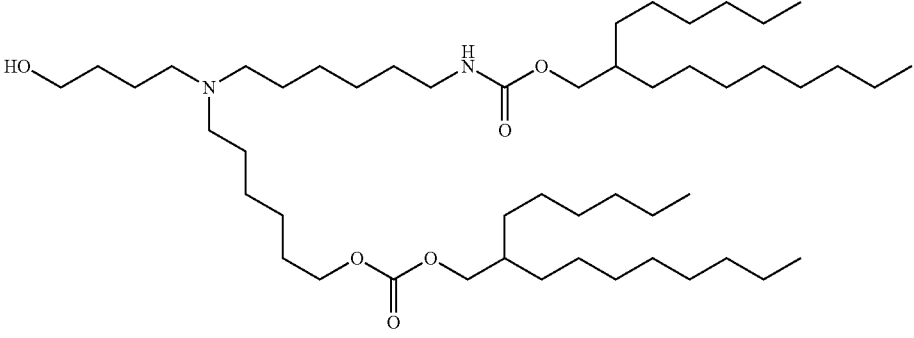 [SMILES: CCCCCCCCC(CCCCCC)COC(=O)NCCCCCCN(CCCCO)CCCCCCOC(=O)OCC(CCCCCC)CCCCCCCC] | 2.57E+08 |
| Sample E-24 | 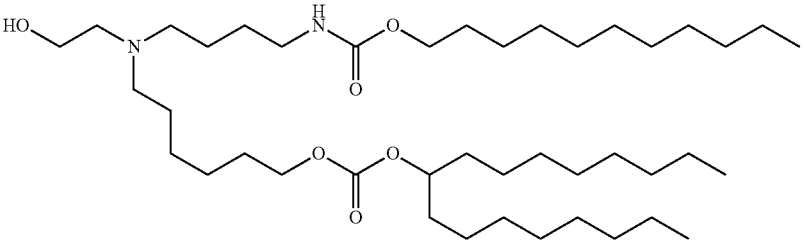 [SMILES: CCCCCCCCCCCOC(=O)NCCCCN(CCO)CCCCCCOC(=O)OC(CCCCCCCC)CCCCCCCC] | 1.83E+08 |
| Sample E-25 | 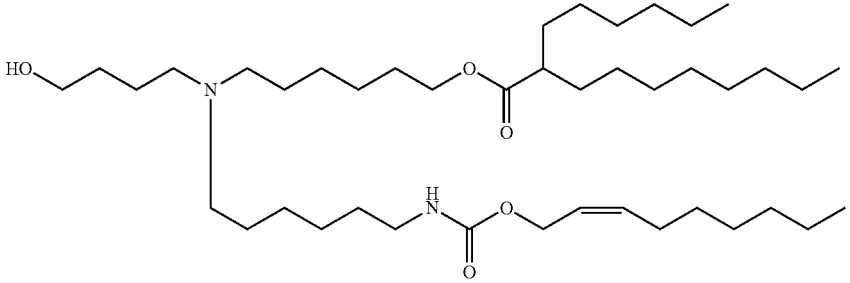 [SMILES: CCCCCC/C=C\COC(=O)NCCCCCCN(CCCCO)CCCCCCOC(=O)C(CCCCCC)CCCCCCCC] | 8.85E+07 |
| Sample E-26 | 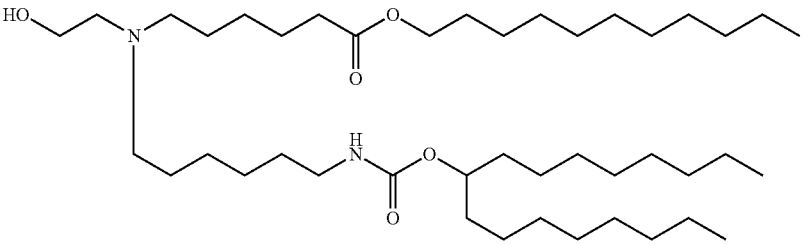 [SMILES: CCCCCCCCCCCOC(=O)CCCCCN(CCO)CCCCCCNC(=O)OC(CCCCCCCC)CCCCCCCC] | 1.62E+08 |

TABLE 2-continued

| mRNA-LNP sample | Structure of lipid compound | Mean intensity (p/s/cm²/sr) |
|---|---|---|
| Sample E-27 | [structure] | 1.62E+08 |
| Sample E-28 | [structure] | 1.16E+07 |

Analysis of the results:

ALC0315 is a commercially available positive control sample. A comparison of the experimental results between the LNP samples containing E-1 to E-28 described in the present invention and ALC0315 revealed that the transfection efficiency of the LNPs prepared with the lipid compounds described in the present invention was significantly higher than that of the commercially available positive control sample, demonstrating remarkable improvement and unexpected effects.

Experiment 3: Biocompatibility Experiment

Cell viability was determined using the CCK-8 (cell counting kit-8) kit. Hep3B cells in exponential growth phase (100 μL, cell density of $2 \times 10^4$ cells/mL) were seeded into a 96-well plate and incubated in a cell culture incubator for 24 hours. After removal of the culture medium from each well, 100 μL of fresh cell culture medium containing mRNA at 20 μg/mL encapsulated in LNPs was added, and the cells were co-incubated for 4 hours. Subsequently, the cell supernatant was removed, fresh cell culture medium was added, and the cells were further incubated for 20 hours. Then, the supernatant was removed, and 100 μL of fresh cell culture medium containing CCK-8 working solution (10 μL/mL) was added and incubated for 2 hours. Blank wells were set up with cell culture medium containing the working solution of CCK-8. The absorbance at 450 nm of each well was measured using a multimode microplate reader (no bubbles should be present in the plate during measurement). Cells without LNPs treatment were used as the control group, and their cell viability was set as 100%.

Cell viability (%)=[$A1-A0$]/[$A2-A0$]×100;

A1 represented the absorbance of the drug-treated group, A0 represented the absorbance of the blank group, and A2 represented the absorbance of the control group. The experimental results were shown in Table 3.

TABLE 3

| mRNA-LNP sample | Cell viability (%) |
|---|---|
| ALC0315 | 94% |
| Sample E-1 | 96% |
| Sample E-2 | 95% |
| Sample E-3 | 94% |
| Sample E-4 | 96% |
| Sample E-5 | 97% |
| Sample E-6 | 98% |
| Sample E-7 | 96% |
| Sample E-8 | 95% |
| Sample E-9 | 96% |
| Sample E-10 | 95% |
| Sample E-11 | 96% |
| Sample E-12 | 95% |
| Sample E-13 | 96% |
| Sample E-14 | 95% |
| Sample E-15 | 96% |
| Sample E-16 | 94% |
| Sample E-17 | 96% |
| Sample E-18 | 96% |
| Sample E-19 | 97% |
| Sample E-20 | 94% |
| Sample E-21 | 96% |
| Sample E-22 | 95% |
| Sample E-23 | 96% |
| Sample E-24 | 97% |
| Sample E-25 | 95% |
| Sample E-26 | 93% |
| Sample E-27 | 95% |
| Sample E-28 | 95% |

The experimental results demonstrated that within the specified concentration range of LNPs, cell viability remained above 90%, with no significant cytotoxicity observed.

Experiment 4: Cryopreservation Stability Experiment of Lipid Nanoparticles

Taking sample E-5 as an example, the LNPs prepared according to the formulation were stored at 4° C. under low-temperature conditions. At different time points (0 day, 6 days, 10 days, 15 days, 30 days, 45 days, 60 days, 90 days), the particle size and PDI of mRNA-LNPs were characterized using Malvern Zetasizer Nano ZS. The encapsulation efficiency of mRNA was determined using the Ribogreen RNA Quantification Assay Kit (Thermo Fisher). The measurement results were shown in Table 4.

TABLE 4

| Cryo-preservation condition | Cryo-preservation time (day) | Size (nm) | PDI | Encapsulation efficiency (%) |
|---|---|---|---|---|
| 4° C. | 0 | 72.1 | 0.092 | 98.6 |
| | 6 | 72.2 | 0.094 | 98.3 |
| | 10 | 72.4 | 0.098 | 97.9 |
| | 15 | 72.2 | 0.101 | 97.2 |
| | 30 | 72.6 | 0.097 | 97.9 |
| | 45 | 72.7 | 0.103 | 97.4 |
| | 60 | 73.1 | 0.107 | 97.4 |
| | 90 | 74.1 | 0.109 | 97.5 |

From Table 4, it could be observed that the LNPs formed by the lipid molecules described in the present invention remained stable in terms of particle size and encapsulation efficiency when stored for 90 days under low-temperature conditions. This facilitated the transportation and storage of the products, making them suitable for industrial production.

Experiment 5: Animal Test of Immune Effects

The materials prepared were as follows: Twenty female Balb/c mice, aged six weeks, weighing 15~20 g each, were housed in experimental conditions at a temperature of 22±2° C. and relative humidity of 45-75%, with a 12-hour light/dark cycle. After purchase, the mice were acclimatized in the animal facility for one week before the commencement of formal animal experiments. The twenty mice were randomly divided into 4 groups as follows: the first group received a volume-matched injection of PBS into the hind leg muscle (negative control group); the second group received a mixture of 10 μg of mRNA, PBS, and the commercial positive control sample ALC-0315 via injection into the hind leg muscle (positive control group); the third group received a mixture of 10 μg of mRNA, PBS, and the experimental sample E-28 via injection into the hind leg muscle (experimental group 1); the fourth group received a mixture of 10 μg of mRNA, PBS, and the experimental sample E-1 via injection into the hind leg muscle (experimental group 2). The mRNA used was synthesized from a self-designed template via in vitro transcription to express the full-length Spike protein.

The experimental procedure was as follows: On days 0 and 14, the LNP mixtures encapsulating mRNA were intramuscularly injected into Balb/c mice according to the aforementioned four groups. Ocular blood samples were collected on days 13 and 21, incubated at 37° C. for 1 hour, and then centrifuged at 3500 rpm for 15 min. The supernatant was collected for analysis. A ELISA assay kit was used to detect the titers of prime vaccination and boost vaccination mouse serum specific antibodies against the Delta variant S1 protein.

The specific procedure for detecting the titers of prime vaccination and boost vaccination mouse serum specific antibodies against the Delta variant S1 protein was as follows: Spike S1 recombinant protein was added to a 96-well plate at a concentration of 0.25 μg per well and incubated at 4° C. overnight. The next day, the liquid in the wells was discarded, and each well was blocked with 200 μL of 5% BSA PBST solution at 37° C. for 1 hour. Subsequently, the liquid in the wells was discarded, and the wells were washed three times with 200 μL of PBST washing solution, with each wash lasting for 3 minutes, followed by air drying. Mouse serum was diluted with PBS (1:20000) or standards were diluted with PBS to a series of concentrations with the stock solution of 1 μg/μL, using half-dilution method, totaling 14 standard curves). Then, 100 μL of the diluted samples and standard curves were added to the wells and incubated at 37° C. for 2 hours. After incubation, the liquid in the wells was discarded, and the wells were washed three times with 200 μL of PBST washing solution, with each wash lasting for 3 minutes, followed by air drying. Subsequently, 100 μL of Goat anti-mouse IgG HRP (diluted 1:5000 in PBS) was added to each well and incubated at 37° C. for 1 hour. The liquid in the wells was then discarded, and the wells were washed three times with 200 μL of PBST washing solution, with each wash lasting for 3 minutes, followed by air drying. TMB substrate A and B solutions were mixed in equal proportions, and 100 μL of the mixture was added to each well and incubated at 37° C. in the dark for several minutes (3-5 minutes). The absorbance was measured at 650 nm, and when the maximum absorbance value was around 1.5, 100 μL of stop solution was added. The absorbance value at 450 nm was measured within 15 minutes after adding the stop solution. The IgG concentration of each group was calculated based on the standard curve formula.

Figure 4:
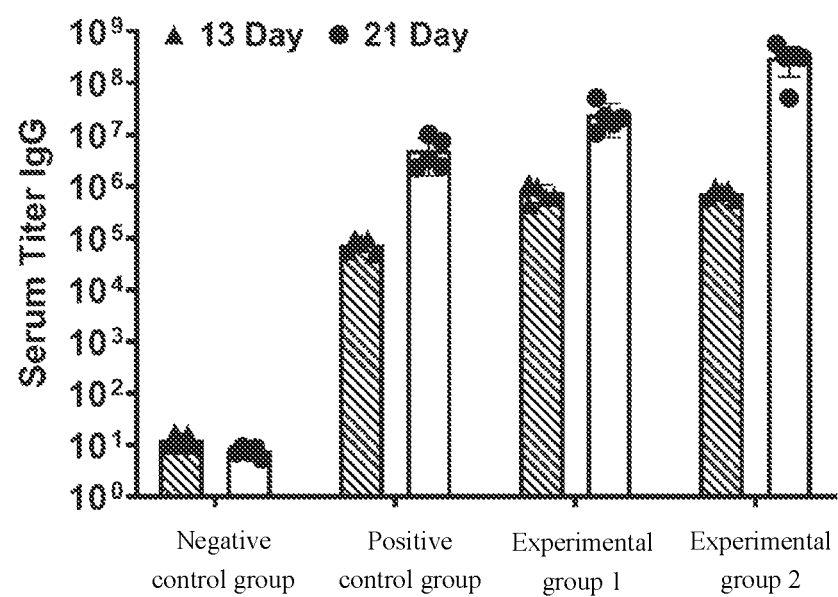
FIG. 4 depicts a schematic diagram of the comparative experimental results of the immune effect of the LNP prepared by the lipid compound described in the present invention and the commercially available LNP.

The experimental results, as illustrated in FIG. 4, indicated that all three groups, including the positive control group and the experimental groups, were able to generate specific antibodies against the S1 protein. Moreover, the antibody titers in the experimental groups were significantly higher than those in the positive control group. This suggested that the experimental groups efficiently delivered mRNA into cells, expressed antigens, thereby triggering an immune response in vivo, resulting in the production of corresponding antibodies, and exhibiting protective functions.

In summary, the novel lipid compounds described in this invention exhibit prominent and substantial characteristics in molecular structures. The aforementioned experiments have demonstrated that the lipid compounds confer capacities of fusing membrane and escaping endosome to the corresponding LNPs. The lipid compounds feature a tertiary amine-containing group in the head structure and two hydrophobic groups in the tail structure. One hydrophobic group is modified with —(C=O)O—, —O(C=O)—, —NH(C=O)O—, —O(C=O) NH— or —O(C=O)O—, while the other one is incorporated with carbamate bond (—NH(C=O)O— or —O(C=O) NH—) as a degradable moiety. Moreover, these lipid compounds described in this invention exhibit better transfection efficacy compared to the LNPs commonly used in the market (Pfizer sample). Taken together, the lipid compounds described in this invention possess novel molecular structures and unexpected technical effects, making this invention non-obvious and inventive.

It should be noted here that the lipid compound described in the present invention is a kind of pharmaceutical raw material, pharmaceutical product, which does not involve the treatment method or diagnostic method of any disease, and belongs to the scope of patentable rights. The scope of application of the present invention is not limited, can be applied in the field of vaccines, as well as in protein replacement therapy, gene editing, cell therapy, and other fields. The examples here are not exhaustive, as long as the lipid compounds that have the structural characteristics described in the present invention fall within the scope of protection of the present invention.

The basic principles, main features, and advantages of the present invention are shown and described herein. Those skilled in the art should understand that the aforementioned embodiments do not limit the present invention in any form, and all technical solutions obtained by means of equivalent substitution or equivalent transformation fall within the scope of protection of the present invention.

The invention claimed is:

1. A lipid compound having a structure of Formula:

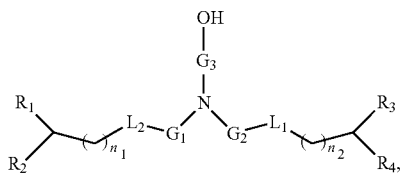

wherein:
$n_1$ and $n_2$ are each independently 0, 1, or 2;
$G_1$ and $G_2$ are each independently C4-C8 alkylene;
$R_1$, $R_2$, $R_3$ and $R_4$ are each independently C1-C12 linear or branched alkyl, or C2-C10 linear or branched alkenyl;
$G_3$ is C2-C5 alkylene; or $G_3$ is $(CH2)_a$—O—$(CH2)_b$, wherein a and b are each independently 2;
$L_1$ is —(C=O)O—, —O(C=O)—, or —O(C=O)O—;
$L_2$ is —NH(C=O)O— or —O(C=O)NH—.

2. The lipid compound of claim 1, wherein each of —CH($R_1$)$R_2$ and —CH($R_3$)$R_4$ is independently selected from the group consisting of

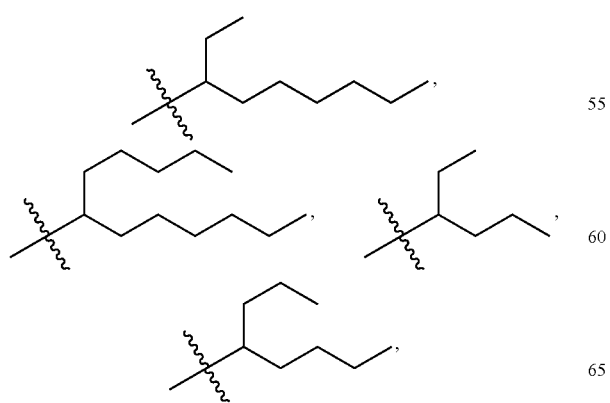

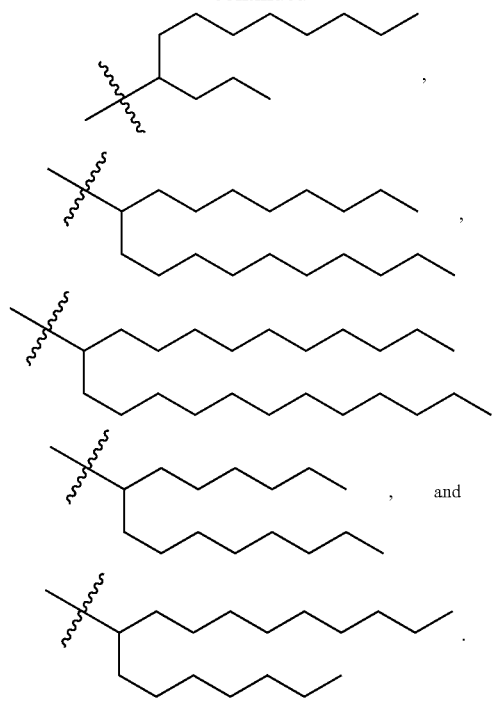

3. The lipid compound of claim 1, wherein each of —CH($R_1$)$R_2$ and —CH($R_3$)$R_4$ is independently selected from the group consisting of

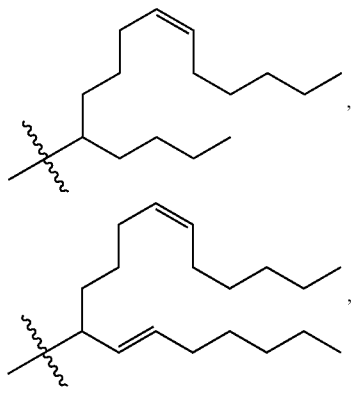

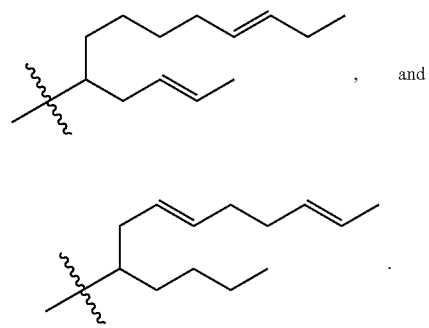

4. The lipid compound of claim 1, wherein the lipid compound is selected from the group consisting of

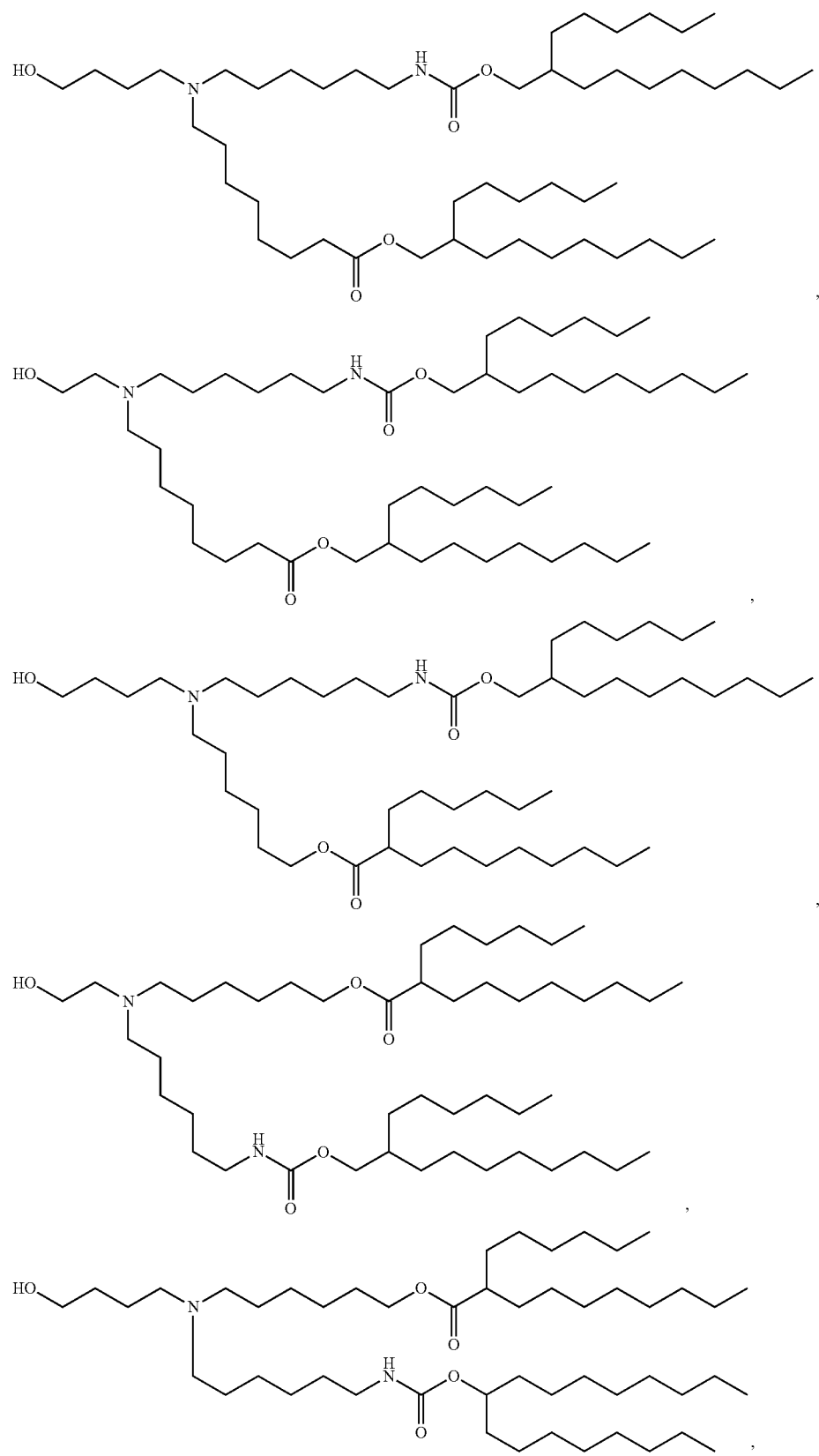

-continued
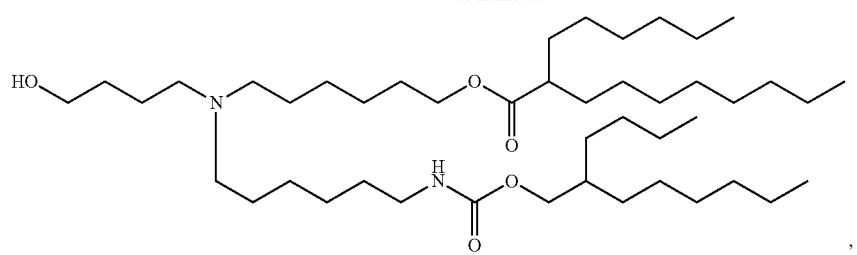
,
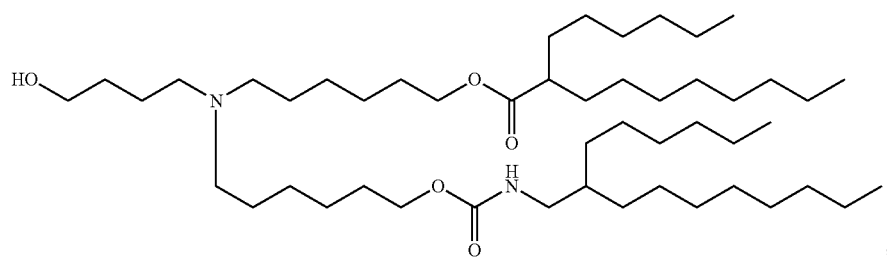
,
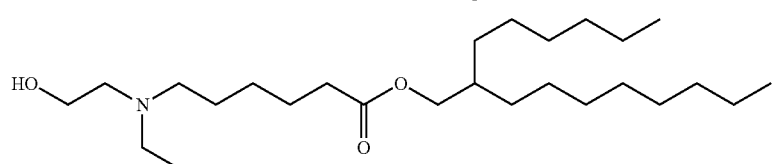
,
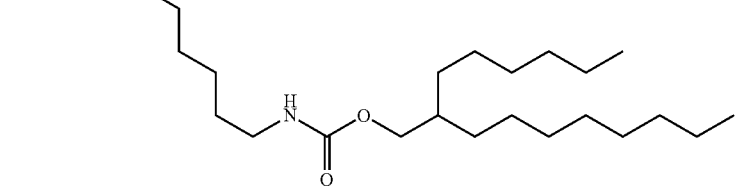
,
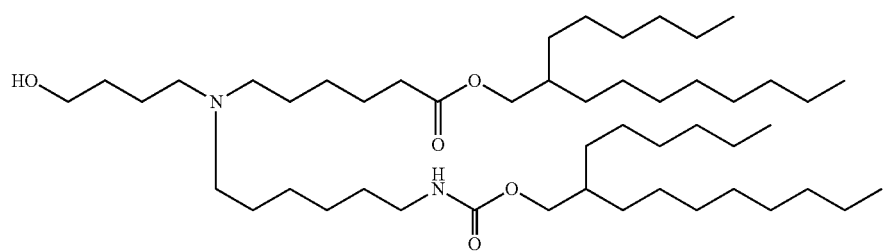
,
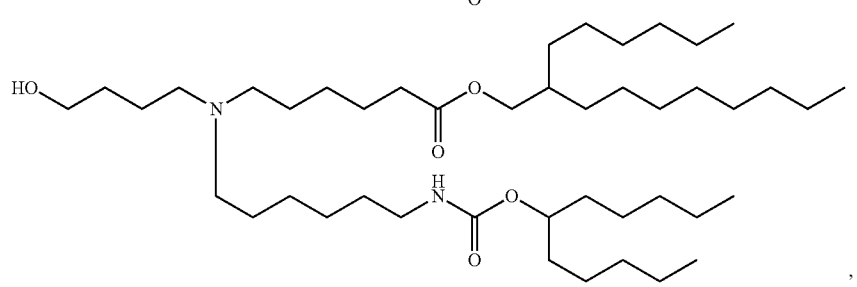
,
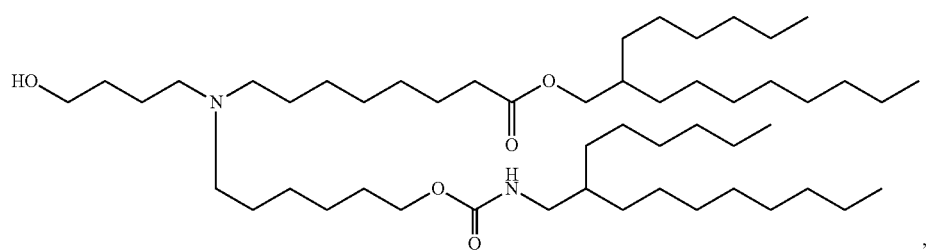
, -continued
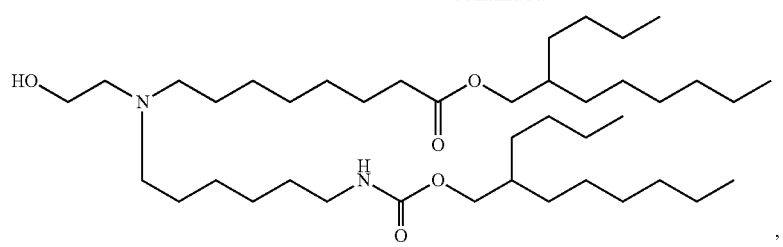
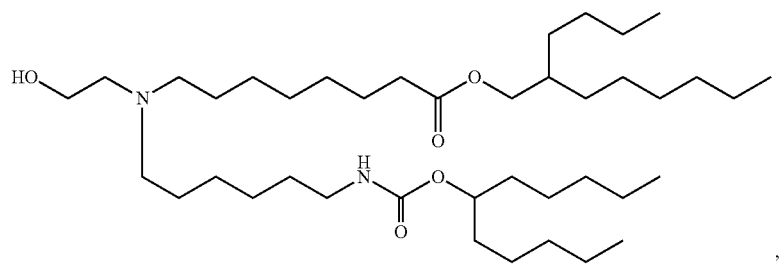
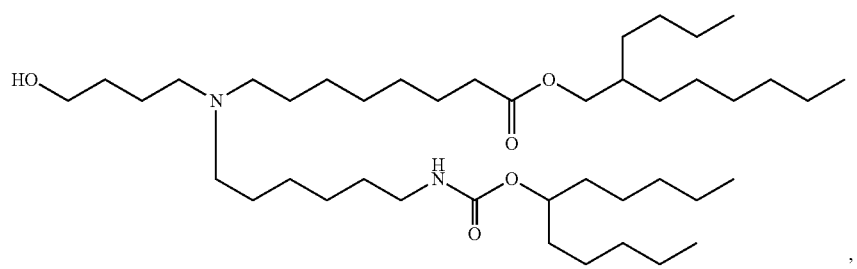
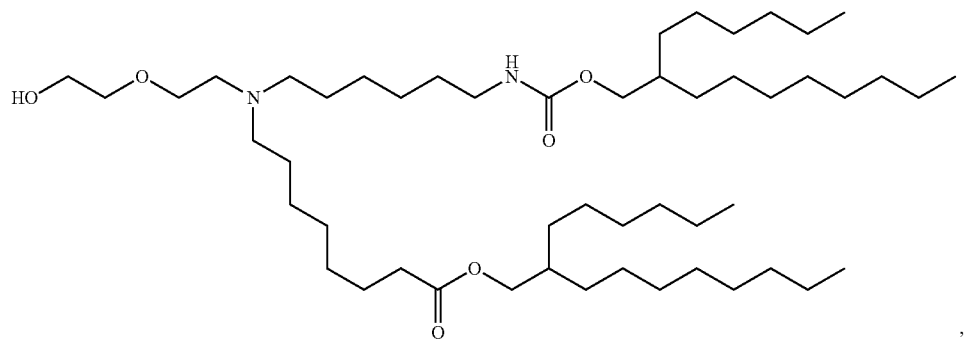
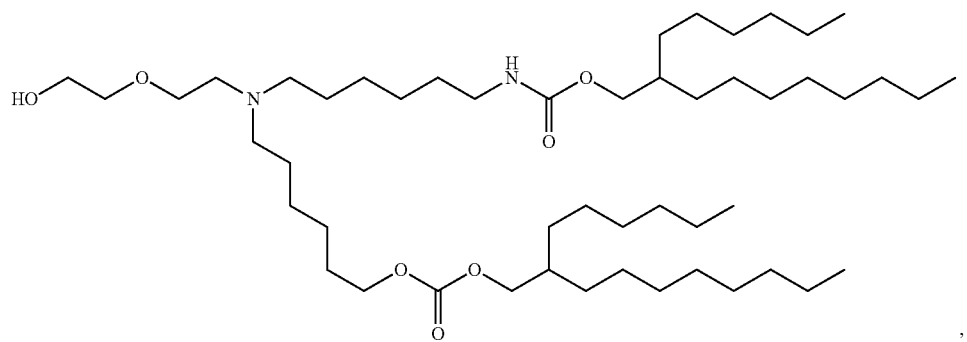

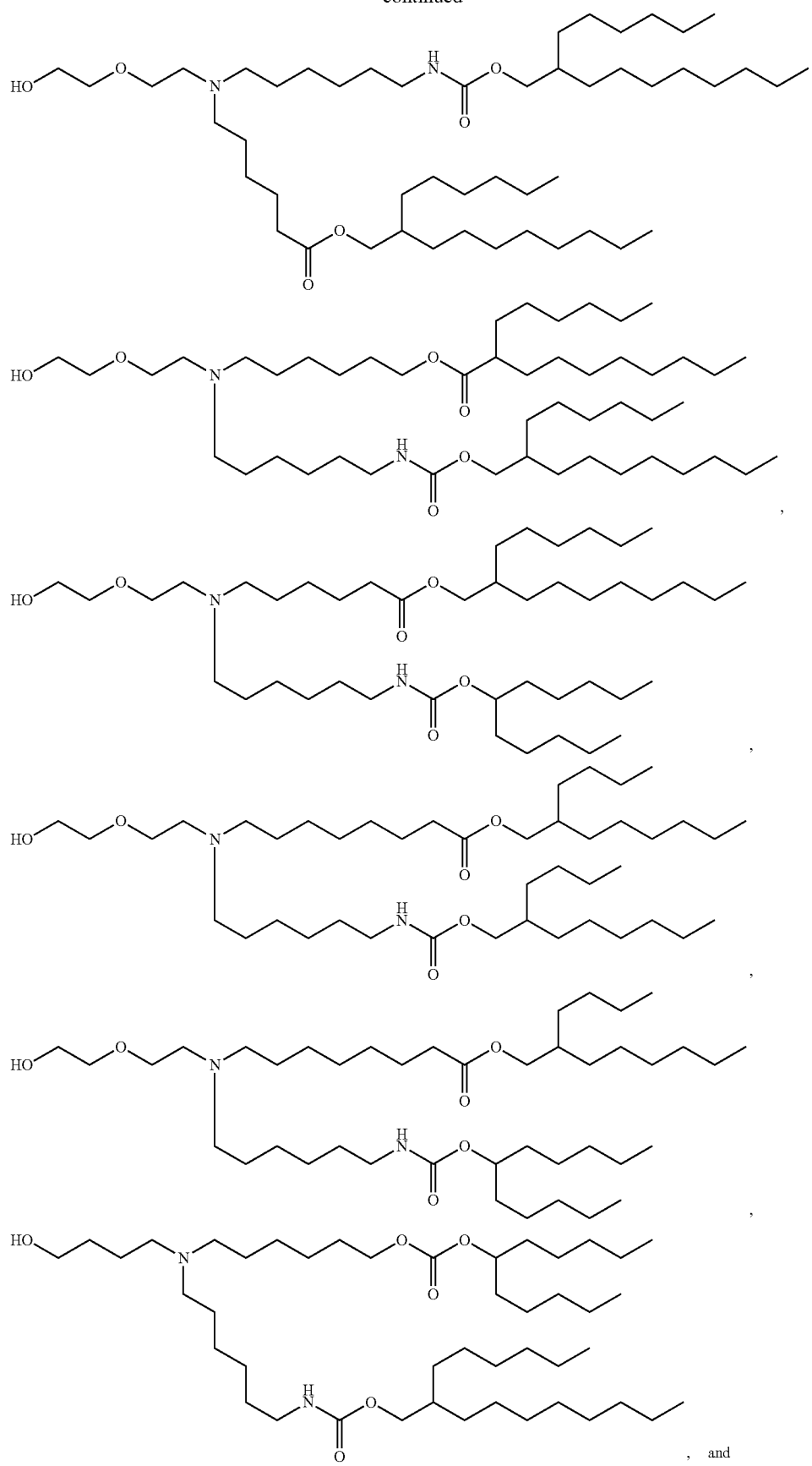

-continued

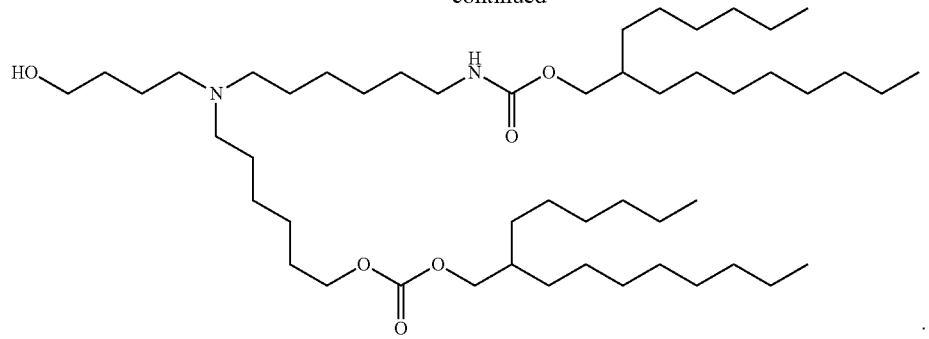

5. A composition comprises the lipid compound of claim 1 or a stereoisomer, tautomer, or pharmaceutically acceptable salt thereof.

6. The composition of claim 5, wherein the composition comprises a carrier, a loaded drug, a pharmaceutical adjuvant, or a combination thereof.

7. The composition of claim 6, wherein the carrier comprises one or more lipid compounds having a structure of Formula:

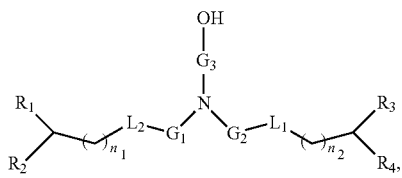

helper lipids, structural lipids, polymer-conjugated lipids or amphiphilic block copolymers, or the combinations thereof, wherein:
- $n_1$ and $n_2$ are each independently 0, 1, or 2;
- $G_1$ and $G_2$ are each independently C4-C8 alkylene;
- $R_1$, $R_2$, $R_3$ and $R_4$ are each independently C1-C12 linear or branched alkyl, or C2-C10 linear or branched alkenyl;
- $G_3$ is C2-C5 alkylene; or $G_3$ is $(CH2)_a$—O—$(CH2)_b$, wherein a and b are each independently 2;
- $L_1$ is —(C=O)O—, —O(C=O)—, — or —O(C=O)O—;
- $L_2$ is —NH(C=O)O— or —O(C=O)NH—.

8. The composition of claim 7, wherein the molar ratio of the lipid compound to the helper lipid ranges from 0.5:1 to 15:1.

9. The composition of claim 7, wherein the molar ratio of the lipid compound to the structural lipid ranges from 0.5:1 to 5:1.

10. The composition of claim 7, wherein the molar ratio of the lipid compound to the polymer-conjugated lipid ranges from 5:1 to 250:1.

11. The composition of claim 7, wherein the molar ratio of the lipid compound to the amphiphilic block copolymer ranges from 1:1 to 200:1.

12. The composition of claim 6, wherein the carrier is lipid nanoparticles, the average size of the lipid nanoparticles ranges from 30 to 200 nm, and the polydispersity index of the lipid nanoparticle is ≤0.3.

13. The composition of claim 6, wherein the loaded drug comprises one or more nucleic acid molecules, small molecule compounds, peptides or proteins, or a combinations thereof.

14. The composition of claim 6, wherein the pharmaceutical adjuvant comprises one or more diluents, stabilizers, preservatives or lyoprotectants, or a combinations thereof.

* * * * *